(12) United States Patent
Ono

(10) Patent No.: US 7,638,025 B2
(45) Date of Patent: Dec. 29, 2009

(54) FLUID HANDLING APPARATUS

(75) Inventor: Koichi Ono, Kawaguchi (JP)

(73) Assignee: Enplas Corporation, Saitama (JP)

( * ) Notice: Subject to any disclaimer, the term of this patent is extended or adjusted under 35 U.S.C. 154(b) by 733 days.

(21) Appl. No.: 11/471,017

(22) Filed: Jun. 19, 2006

(65) Prior Publication Data

US 2007/0000541 A1    Jan. 4, 2007

(30) Foreign Application Priority Data

Jun. 17, 2005  (JP)  ............................. 2005-177336
Jul. 14, 2005  (JP)  ............................. 2005-205712

(51) Int. Cl.
  *C25B 13/02*  (2006.01)
  *G01N 13/02*  (2006.01)
  *F15C 1/04*  (2006.01)

(52) U.S. Cl. ..................... 204/601; 204/451; 422/68.1; 422/81; 422/99; 422/100; 422/103; 137/814; 137/833

(58) Field of Classification Search ................ 204/451, 204/601; 422/68.1, 81, 99, 100, 102, 103
See application file for complete search history.

(56) References Cited

U.S. PATENT DOCUMENTS 4,983,038 A * 1/1991 Ohki et al. ................... 356/246
7,338,584 B2 * 3/2008 Ono ............................. 204/604

2004/0184964 A1 * 9/2004 Watanabe et al. ............ 422/100
2005/0019794 A1   1/2005 Nassef et al.
2007/0199603 A1 * 8/2007 Ono ............................. 137/833

FOREIGN PATENT DOCUMENTS

JP  2004-163104  6/2004
JP  2005-114433  4/2005

OTHER PUBLICATIONS

Single Step Concentration and Sequence-Specific Separation of DNA By Affinity Microchip Electrophoresis (8th International Conference on Miniaturized Systems For Chemistry and Life Sciences, Sep. 26-30, 2004.

* cited by examiner

*Primary Examiner*—Bruce F Bell
(74) *Attorney, Agent, or Firm*—Bachman & LaPointe, P.C.

(57) ABSTRACT

When a first liquid fed into a first flow passage 6 moves therein toward a connecting portion 10 due to capillarity, gas in the first flow passage 6 is pushed by the moving first liquid to be exhausted to the external environment via a third flow passage 14 and an external environment communication passage 8, so that the first liquid moves to the end of a fifth flow passage 16, which is formed in the connecting portion 10, on the side of a second flow passage 7 due to capillarity. Then, when a second liquid fed into the second flow passage 7 moves therein toward the connecting portion 10 due to capillarity, gas in the second flow passage 7 is pushed by the moving second liquid to be exhausted to the external environment via a fourth flow passage 15 and the external environment communication passage 8, so that a liquid-liquid interface level between the first and second liquids is formed in the connecting portion 10.

11 Claims, 25 Drawing Sheets

FLUID HANDLING APPARATUS

BACKGROUND OF THE INVENTION

1. Field of the Invention

The present invention generally relates to a fluid handing apparatus. More specifically, the invention relates to a fluid handing apparatus for forming a liquid-liquid interface level in a connecting portion in which a flow passage is connected to another flow passage (i.e., in a junction between flow passages), and a fluid handling apparatus for forming a liquid-liquid interface level in each of a plurality of connecting portions, in each of which a flow passage is connected to another flow passage, to meter a very small amount of liquid between the connecting portions and/or to move a charged material in a metered liquid by electrophoresis.

2. Description of the Prior Art

There is known a fluid handling apparatus for efficiently carrying out the crystallization of a protein by the moving boundary diffusion method (or carrier-free diffusion method) via a liquid-liquid interface level formed between a reagent and a solution of the protein by opening a shut-off valve by which a first flow passage containing the reagent is separated from a second flow passage containing the solution of the protein. In such a fluid handling apparatus, a pressure passage for operating a shut-off valve is arranged so as to be close to a flow passage, and a part of the wall of the flow passage is elastically deformed by the pressure of a fluid in the pressure passage for closing the flow passage (see, e.g., U.S. Patent Publication No. 2005/0019794).

However, such a conventional fluid handling apparatus has a complicated structure and is required to have a pressurizing means, since the shut-off valve is formed in a fine flow passage (or microchannel). Therefore, there is a problem in that the whole structure of the apparatus including the pressurizing means is large.

There has been developed a fluid handling apparatus for metering a very small amount of liquid, which contains an analyzing object (a target material) such as a protein or a nucleic acid in an organism, in a flow passage to move the very small amount of liquid due to electrophoresis to detect and analyze the analyzing object in the liquid by means of a measuring device which is arranged in the flow passage.

FIGS. 19A through 19F show a first example of such a conventional fluid handling apparatus. The conventional fluid handling apparatus 100 shown in FIGS. 19A through 19F is made of polydimethylsiloxane (PDMS) which is a material having a high gas permeability, and comprises: a first linear flow passage 101 for moving a liquid sample containing an analyzing object (protein, nucleic acid, DNA or the like) due to electrophoresis; a second flow passage 102 serving as a sample feeding passage which is connected to the middle of the first flow passage so as to be orthogonal thereto; and ports 103, 104 and 105 which are formed in both end portions of the first flow passage 101 and the end portion of the second flow passage 102, respectively. The first flow passage 101 of the fluid handling apparatus 100 has a pair of stop valves 106a and 106b for abruptly decreasing the flow passage area (cross-sectional area) of the first flow passage 101 to dam the stream of a liquid. As shown in FIG. 19A, between the stop valves 106a and 106b, the second flow passage 102 is connected to the first flow passage 101 near the stop valve 106a upstream in electrophoresis directions (on the left side in FIGS. 19A through 19F).

As shown in FIG. 19B, the fluid handling apparatus 100 with this construction is housed in a vacuum equipment 107 to exhaust gas in the fluid handling apparatus 100 (including gas in the first and second flow passages 101 and 102). Then, as shown in FIG. 19C, after the first and second flow passages 101 and 102 are in a vacuum state, a liquid sample 110 containing DNA is dropped into the port 105 which is arranged in the end portion of the second flow passage 102, and polymer solutions 111 and 112 are dropped into the ports 103 and 104 which are arranged in both end portions of the first flow passage 101, respectively. Then, as shown in FIG. 19D, the sample 110 is sucked (fed) by a negative pressure into the first flow passage 101 between the pair of stop valves 106a and 106b via the second flow passage 102. In addition, the polymer solution 111 is sucked (fed) by a negative pressure into the first flow passage 101 between the port 103 and the stop valve 106a, and the polymer solution 112 is sucked by a negative pressure into the first flow passage 101 between the port 104 and the stop valve 106b, so that the first flow passage 101 is filled with the polymer solutions 111, 112 and the sample 110.

If the fluid handling apparatus 100 is designed so that the first flow passage 101 has a desired volume between the pair of stop valves 106a and 106b, it is possible to meter a desired amount of sample 110. Then, electrodes are arranged in the ports 103 and 104, which are arranged in both end portions of the first flow passage 101, and in the port 105 which is arranged in the end portion of the second flow passage 102. Then, a voltage is applied to the liquids (the polymer solutions 111, 112 and the sample 110) in the first flow passage and second flow passage 102 to return the analyzing object, which is arranged in the second flow passage 102, toward the port 105 (see FIGS. 19E and 19F), and to cause the analyzing object, which is contained in the sample 110 in the first flow passage 101, to move in the first flow passage 101 beyond the stop valve 106b (the right stop valve in the figure) to the right (in the direction of D in the figure) due to electrophoresis, so that only a predetermined amount of analyzing object arranged between the stop valves 106a and 106b can be accurately analyzed by means of a measuring device arranged between the stop valve 106b and the port 104 (see, e.g., "SINGLE-STEP CONCENTRATION AND SEQUENCE-SPECIFIC SEPARATION OF DNA BY AFFINITY MICROCHIP ELECTROPHORESIS", 8th International Conference on Miniaturized Systems for Chemistry and Life Sciences, Sep. 26-30, 2004).

However, in the above described first example of the conventional fluid handling apparatus 100, it is required to exhaust gas in the flow passages (the first and second flow passages 101, 102) in the vacuum equipment 107, so that there are problems in that the apparatus is large and it takes a lot of time to carry out a pretreatment (a preliminary work before the start of a sample analyzing operation).

FIGS. 20A through 20D show a second example of a conventional fluid handling apparatus. The fluid handling apparatus 200 shown in FIGS. 20A through 20D has flow passages C and D for connecting parallel flow passages A and B to each other. The flow passage area of the flow passage D is abruptly decreased so as to be a far smaller flow passage area than that of the flow passages A, B and C. To the flow passage D, a degassing flow passage E is connected. Among these flow passages A through E, the wall surface of the flow passage D is difficult to be wet (easy to cause repulsion in capillary tube), so that a liquid can not move in the flow passage D due to capillarity. On the other hand, the wall surfaces of the flow passages A and C are easy to be wet (easy to cause capillarity), and the flow passage area of the flow passage C is smaller than that of the flow passage A.

Thus, if a liquid sample 201 is fed into the flow passage A of the fluid handling apparatus 200, the sample 201 in the flow passage A is sucked into the flow passage C due to capillarity. However, the sample 201 entering the flow passage C is dammed (or stopped) by the flow passage D, so that a predetermined amount of sample 201 is metered in the flow passage C (see FIG. 20B). Furthermore, since a polymer solution 202 for moving an analyzing object, which is contained in the sample 201, due to electrophoresis is filled in the flow passage B, the sample 201 in the flow passage A can not be fed into the flow passage C due to capillarity if gas is contained in the flow passage C. Therefore, when the sample 201 in the flow passage A is fed into the flow passage C, the flow passage E is open to exhaust gas in the flow passage C to the outside via the flow passage E.

In such a state, a pressure (gas pressure) at a first stage is applied to the flow passage A to such an extent that the sample 201 in the flow passage C does not escape from the flow passage D toward the flow passage B and that the sample 201 in the flow passage A is moved downstream (to the right in the figure) of the connecting portion of the flow passage A to the flow passage C, so that a predetermined amount of sample 201 is metered in the flow passage C (see FIG. 20C). Thereafter, a pressure (gas pressure) at a second stage, which is a higher pressure than the pressure at the first stage, is applied to the flow passages A and C to such an extent that the sample 201 in the flow passage C passes through the flow passage D to the flow passage B. As a result, the sample 201 in the flow passage C moves into the flow passage B via the flow passage D (see FIG. 20D). Furthermore, when the sample 201 in the flow passage C is moved toward the flow passage B via the flow passage D, the degassing flow passage E is closed.

Then, a voltage is applied to both ends of the flow passage B to move the analyzing object of the sample 201, which is fed into the flow passage B from the flow passage C via the flow passage D, due to electrophoresis (see, e.g., Japanese Patent Laid-Open No. 2004-163104).

However, in the above described second example of the conventional fluid handling apparatus 200, the flow passage E is closed when the sample 201 in the flow passage C is moved to the flow passage B via the flow passage D, so that there is the possibility that gas remaining in the flow passage D is mixed with the sample 201 in the flow passage B to prevent the sample 201 from being smoothly moved by electrophoresis. In addition, since pressures at two stages must be applied to the flow passage A in the fluid handling apparatus 200, operation is complicated. Moreover, since a pressurizing means must be connected to the flow passage A, the structure of the apparatus is complicated, and the whole structure including the pressurizing means and so forth is large.

As a third example of a conventional fluid handling apparatus for use in the analysis of a sample such as a protein or nucleic acid, there has been developed a fluid handling apparatus (a chip for electrophoresis) capable of accurately metering a very small amount of sample, which is required to carry out analysis, to quantitatively analyzing the sample. Such a fluid handling apparatus uses a gas control device for preventing gas from remaining in a flow passage, so that it is possible to form a sample piece, which contacts a buffer solution on a liquid-liquid interface level, in a flow passage for electrophoresis (see, e.g., Japanese Patent Laid-Open No. 2005-114433).

However, in order to exhaust gas from the third example of the conventional fluid handling apparatus, it is required to control positive/negative pressure by the gas control device, so that operation is complicated. In addition, there is a problem in that the structure of the whole apparatus including the gas control device is complicated and large.

SUMMARY OF THE INVENTION

It is therefore an object of the present invention to eliminate the aforementioned problems and to provide a fluid handling apparatus with a simple and compact structure, which is capable of simply forming a liquid-liquid interface level between a first liquid and a second liquid.

It is another object of the present invention to provide a fluid handling apparatus with a simple and compact structure, which is capable of metering a predetermined amount of sample in a short time and of smoothly analyzing the sample by electrophoresis, while preventing gas from entering the apparatus and without the need of any intentional pressure control from the outside.

In order to accomplish the aforementioned and other objects, according to one aspect of the present invention, a fluid handling apparatus comprises: a first flow passage capable of moving a first fluid due to capillarity; a second flow passage capable of moving a second fluid due to capillarity; and a connecting portion for allowing the first flow passage, the second flow passage and an external environment to be communicated with each other, the connecting portion comprising: a third flow passage for allowing the first flow passage to be communicated with the external environment, the third flow passage being formed so as to be capable of moving the first fluid due to capillarity; a fourth flow passage for allowing the second flow passage to be communicated with the external environment, the fourth flow passage being formed so as to be capable of moving the second fluid due to capillarity; and a fifth flow passage for allowing the first flow passage to be communicated with the second flow passage, the fifth flow passage having a smaller flow passage area than that of each of the first and second flow passages, and the fifth flow passage being formed so as to be capable of moving the first fluid or the second fluid due to capillarity, wherein an interface between the first fluid, which moves in the first flow passage toward the connecting portion, and the second fluid, which moves in the second flow passage toward the connecting portion, is formed in the connecting portion.

In this fluid handling apparatus, the fifth flow passage may allow the first flow passage, the second flow passage and the external environment to be communicated with each other.

According to another aspect of the present invention, a fluid handling apparatus comprises: a first flow passage capable of moving a first fluid due to capillarity; a second flow passage capable of moving a second fluid due to capillarity; and a connecting portion for allowing the first flow passage, the second flow passage and an external environment to be communicated with each other, the connecting portion comprising: a fourth flow passage for allowing the second flow passage to be communicated with the external environment, the fourth flow passage being formed so as to be capable of moving the second fluid due to capillarity; and a fifth flow passage for allowing the first flow passage to be communicated with the second flow passage, the fifth flow passage having a smaller flow passage area than that of the second flow passage, and the fifth flow passage being formed so as to be capable of moving the first fluid due to capillarity, wherein an interface between the first fluid, which is injected into the first flow passage to be moved therein toward the connecting portion, and the second fluid, which is injected into the second flow passage after the injection of the first fluid to be moved therein toward the connecting portion, is formed in the connecting portion.

In the above described fluid handling apparatus, the first flow passage may have a first port for feeding the first fluid into the first flow passage, and the second flow passage may have a second port for feeding the second fluid into the second flow passage.

In the above described fluid handling apparatus according to the present invention, a first fluid in a first flow passage and a second fluid in a second flow passage can move toward a connecting portion in the first and second flow passages, respectively, due to capillarity to easily form a liquid-liquid interface level in the connecting portion, so that it is not required to provide any valve structure which is opened and closed by pressure. Therefore, it is possible to simplify the structure of the apparatus, and it is possible to miniaturize the whole structure of the apparatus.

According to a further aspect of the present invention, a fluid handling apparatus comprises: a first main flow passage capable of moving a first fluid due to capillarity; a second main flow passage capable of moving a second fluid due to capillarity; a third main flow passage capable of moving a third fluid due to capillarity; a first connecting portion for allowing the first main flow passage, the second main flow passage and an external environment to be communicated with each other; and a second connecting portion for allowing the first main flow passage, the third main flow passage and the external environment to be communicated with each other, the first connecting portion comprising: a first sub-flow passage for allowing the first main flow passage to be communicated with the external environment, the first sub-flow passage being formed so as to be capable of moving the first fluid due to capillarity; a second sub-flow passage for allowing the second main flow passage to be communicated with the external environment, the second sub-flow passage being formed so as to be capable of moving the second fluid due to capillarity; and a third sub-flow passage for allowing the first main flow passage to be communicated with the second main flow passage, the third sub-flow passage having a smaller flow passage area than that of each of the first and second main flow passages, and the third sub-flow passage being formed so as to be capable of moving the first fluid or the second fluid due to capillarity, and the second connecting portion comprising: a fourth sub-flow passage for allowing the first main flow passage to be communicated with the external environment, the fourth sub-flow passage being formed so as to be capable of moving the first fluid due to capillarity; a fifth sub-flow passage for allowing the third main flow passage to be communicated with the external environment, the fifth sub-flow passage being formed so as to be capable of moving the third fluid due to capillarity; and a sixth sub-flow passage for allowing the first main flow passage to be communicated with the third main flow passage, the sixth sub-flow passage having a smaller flow passage area than that of each of the first and third main flow passages, and the sixth sub-flow passage being formed so as to be capable of moving the first fluid or the third fluid due to capillarity, wherein an interface between the first fluid, which moves in the first main flow passage toward the first connecting portion, and the second fluid, which moves in the second main flow passage toward the first connecting portion, is formed in the first connecting portion, and an interface between the first fluid, which moves in the first main flow passage toward the second connecting portion, and the third fluid, which moves in the third main flow passage toward the second connecting portion, is formed in the second connecting portion, the first fluid being metered between the first connecting portion and the second connecting portion.

In this fluid handling apparatus, the third sub-flow passage may allow the first main flow passage, the second main flow passage and the external environment to be communicated with each other, the third sub-flow passage being formed so as to be capable of moving at least one of the first and second fluids. In this case, the sixth sub-flow passage may allow the first main flow passage, the third main flow passage and the external environment to be communicated with each other, the sixth sub-flow passage being formed so as to be capable of moving at least one of the first and third fluids. In addition, the first main flow passage may have a first port for feeding the first fluid into the first main flow passage, the second main flow passage having a second port for feeding the second fluid into the second main flow passage, and the third main flow passage having a third port for feeding the third fluid into the third main flow passage. In this case, the first port may be arranged in the vicinity of the first connecting portion or the second connecting portion. The fluid handling apparatus may further comprise a potential difference applying means for applying a potential difference between the second main flow passage and the third main flow passage, to move a charged material, which is contained in the first fluid in the first main flow passage, to the second main flow passage or the third main flow passage due to electrophoresis.

In the above described fluid handling apparatus according to the present invention, a liquid-liquid interface level between a first fluid fed into a first main flow passage and a second fluid fed into a second main flow passage is formed in a first connecting portion, and a liquid-liquid interface level between the first fluid fed into the first main flow passage and a third fluid fed into a third main flow passage is formed in a second connecting portion, so that it is possible to simply meter a desired amount of only the first fluid in the first main flow passage in accordance with the volume of the first main flow passage without intentionally applying pressure from the outside. Therefore, according to the present invention, it is not required to provide any vacuum equipment and pressure control means, and it is possible to simplify the structure of the apparatus and miniaturize the whole structure of the apparatus. In addition, according to the present invention, it is not required to carry out a pretreatment by a vacuum equipment, and it is not required to control pressure in the fluid passage by pressure control means, so that it is possible to remarkably shorten the time to analyze a fluid due to electrophoresis.

In the above described fluid handling apparatus according to the present invention, if a first fluid fed into a first main flow passage reaches a first connecting portion, gas in the first main flow passage is pushed by the first fluid to be exhausted to the external environment via a first sub-flow passage and to be exhausted to the external environment via the third sub-flow passage, second main flow passage and second sub-flow passage. In addition, if the first fluid fed into the first main flow passage reaches a second connecting portion, gas in the first main flow passage is pushed by the first fluid to be exhausted to the external environment via a fourth sub-flow passage and to be exhausted to the external environment via a sixth sub-flow passage, third main-flow passage and fifth sub-flow passage. Thereafter, if a second fluid is fed into the second main flow passage, gas in the second main flow passage is pushed by the second fluid, which moves due to capillarity, to be exhausted to the external environment via the second sub-flow passage. As a result, a liquid-liquid interface level between the second fluid in the second main flow passage and the first fluid in the third sub-flow passage can be formed in the first connecting portion while preventing gas from remaining therein. In addition, if a third fluid is fed into the third main flow passage, gas in the third main flow passage is pushed by the third fluid, which moves due to capillarity, to be exhausted to the external environment via the fifth sub-flow passage. As a result, a liquid-liquid interface level between the third fluid in the third main flow passage and the first fluid in the sixth sub-flow passage can be formed in the second connecting portion while preventing gas from remaining therein. Therefore, according to the present invention, when a potential difference is applied between the second main flow passage and the third main flow passage for causing the first fluid in the first main flow passage to move in the second or third main flow passage due to electrophoresis, it is possible to smoothly and accurately analyze the first fluid due to electrophoresis without causing defective electrophoresis due to bubbles of remaining gas.

If the third sub-flow passage in the first connecting portion allows the first main flow passage, the second main flow passage and the external environment to be communicated with each other, even if the first and second fluids simultaneously reach the first connecting portion, gas pushed by the first and second fluids can be exhausted to the external environment, so that the first and second fluids can be moved by capillarity to form a liquid-liquid interface level therein.

If the sixth sub-flow passage in the second connecting portion allows the first main flow passage, the third main flow passage and the external environment to be communicated with each other, even if the first and third fluids simultaneously reach the second connecting portion, gas pushed by the first and third fluids can be exhausted to the external environment, so that the first and third fluids can be moved by capillarity to form a liquid-liquid interface level therein.

The liquid-liquid interface level between the first and second fluids can be formed at the end of the third sub-flow passage on the side of the first or second main flow passage in the first connecting portion. In addition, the liquid-liquid interface level between the first and third fluids can be formed at the end of the sixth sub-flow passage on the side of the first or third main flow passage in the second connecting portion.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the Drawings:

FIGS. 1A through 1E show the first preferred embodiment of a fluid handling apparatus according to the present invention, wherein FIG. 1A is a plan view of the fluid handling apparatus, FIG. 1B being a front view of the apparatus, FIG. 1C being a left side view of the apparatus, FIG. 1D being a right side view of the apparatus, and FIG. 1E being an enlarged sectional view taken along line IE-IE in FIG. 1B;

FIGS. 3A through 3E show the second preferred embodiment of a fluid handling apparatus according to the present invention, wherein FIG. 3A is a plan view of the fluid handling apparatus, FIG. 3B being a front view of the apparatus, FIG. 3C being a left side view of the apparatus, FIG. 3D being a right side view of the apparatus, and FIG. 3E being an enlarged sectional view taken alone line IIIE-IIIE in FIG. 3B;

FIGS. 5A through 5E show the third preferred embodiment of a fluid handling apparatus according to the present invention, wherein FIG. 5A is a plan view of the fluid handling apparatus, FIG. 5B being a front view of the apparatus, FIG. 5C being a left side view of the apparatus, FIG. 5D being a right side view of the apparatus, and FIG. 5E being an enlarged sectional view taken along line VE-VE in FIG. 5B;

FIGS. 11A through 11C show the fourth preferred embodiment of a fluid handling apparatus according to the present invention, wherein FIG. 11A is a plan view of the fluid handling apparatus, FIG. 11B being a side view of the apparatus, and FIG. 11C being a sectional view taken along line XIC-XIC in FIG. 11A;

DESCRIPTION OF THE PREFERRED EMBODIMENTS

Referring now to the accompanying drawings, the preferred embodiments of a fluid handling apparatus according to the present invention will be described below in detail.

First Preferred Embodiment

Figure 1A:
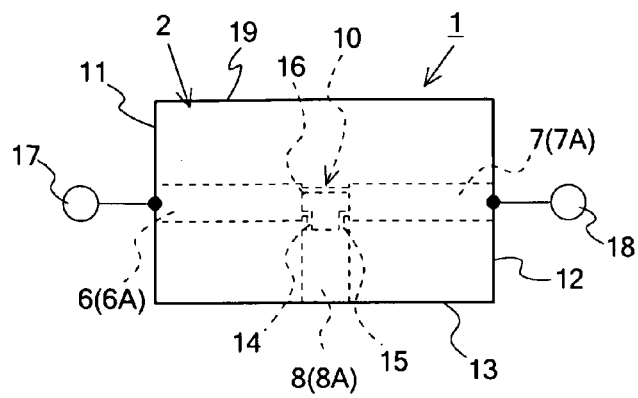
Figure 1C:
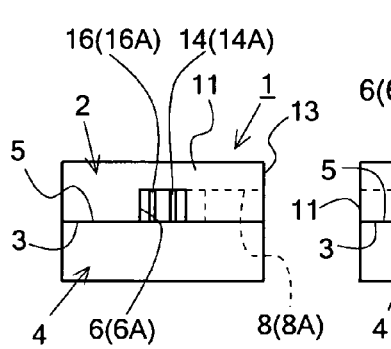
Figure 1B:
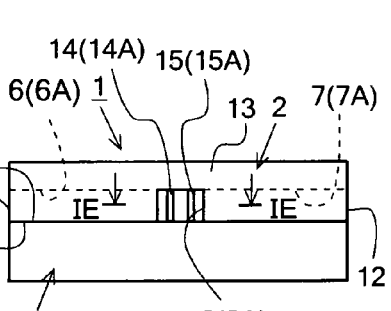
Figure 1D:
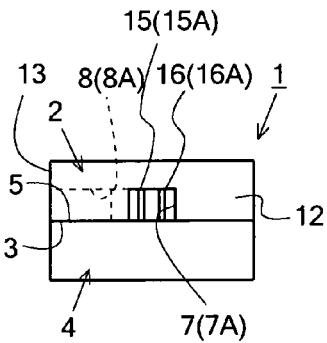
Figure 1E:
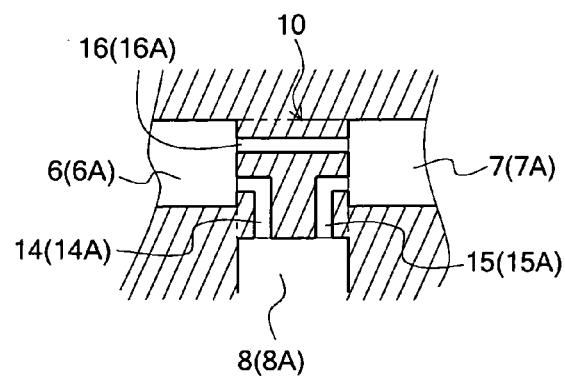

FIGS. 1A through 1E show the first preferred embodiment of a fluid handling apparatus 1 according to the present invention. FIG. 1A is a plan view of the fluid handling apparatus 1, and FIG. 1B is a front view of the fluid handling apparatus 1. FIG. 1C is a left side view of the fluid handling apparatus 1, and FIG. 1D is a right side view of the fluid handling apparatus 1. FIG. 1E is a sectional view taken along line IE-IE in FIG. 1B.

As shown in FIGS. 1A through 1E, the fluid handling apparatus 1 in this preferred embodiment comprises a first sheet-like member 2 having a rectangular planar shape, and a second sheet-like member 4 arranged so as to cover the whole reverse 3 of the first member 2. The first member 2 and the second member 4 are made of any one of various resin materials, such as polymethyl methacrylate (PMMA), polycarbonate (PC) and ultraviolet curable resins, glasses and ceramics. The piled surfaces (facing surfaces) of the first and second members 2 and 4 (the reverse 3 of the first member 2 and the surface 5 of the second member 4 (see FIGS. 2A and 2B)) are smoothed flat surfaces having a good adhesion. The first member 2 is piled on the second member 4 so that the reverse 3 of the first member 2 closely contacts the surface 5 of the second member 4. In this state, the first member 2 is detachably or undetachably fixed to the second member 4 by means of an adhesion, fasteners, clips or the like. Furthermore, while the first member 2 and the second member 4 have been sheet-like members in this preferred embodiment, the present invention should not be limited thereto, but they may be cubic block-shaped members. Alternatively, the second member 4 to be piled on the reverse 3 of the first member 2 may be a film-like member.

Figure 2A:
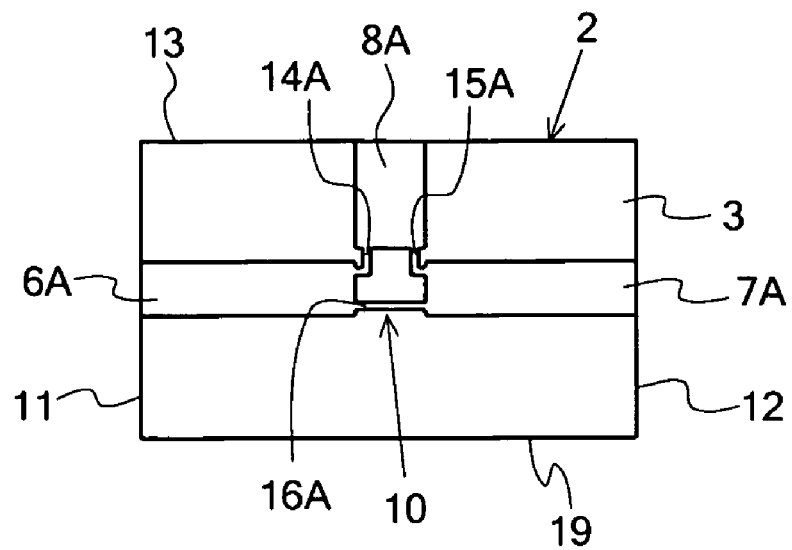
FIG. 2A is a bottom view of a first member of the fluid handling apparatus of FIGS. 1A through 1E.
Figure 2B:
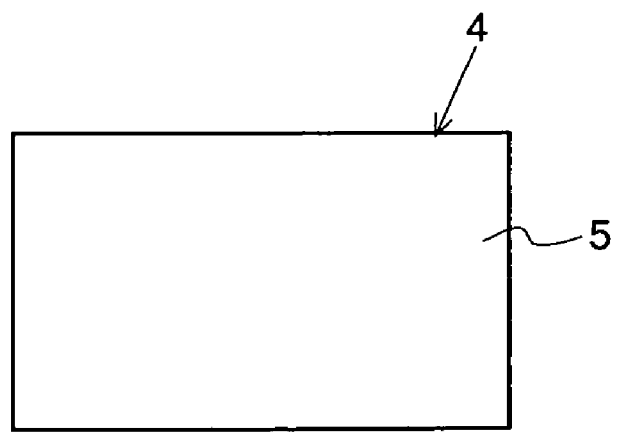
FIG. 2B is a plan view of a second member of the apparatus.

FIG. 2A is a bottom view of the first member 2. As shown in FIG. 2A, a first groove 6A for a first flow passage 6, a second groove 7A for a second flow passage 7, and an external communication groove 8A for an external environment communication passage 8 are formed in the reverse 3 of the first member 2 so as to be connected to each other by a connecting portion 10. Each of the first groove 6A, the second groove 7A and the external communication groove 8A has a rectangular cross section perpendicular to the stream of a fluid flowing therein (see FIGS. 1B, 1C and 1D). The first groove 6A is open on the side of the reverse 3 of the first member 2, and is open on the side of the left side surface 11 of the first member 2 (see FIG. 1C). The second groove 7A is open on the side of the reverse 3 of the first member 2, and is open on the side of the right side surface 12 of the first member 2 (see FIG. 1D). The external communication groove 8A is open on the side of the reverse 3 of the first member 2, and is open on the side of the front side surface 13 of the first member 2 (see FIG. 1B).

As shown in FIGS. 1E and 2A, the connecting portion 10 has a third groove 14A for allowing the first groove 6A to be communicated with the external communication groove 8A, a fourth groove 15A for allowing the second groove 7A to be communicated with the external communication groove 8A, and a fifth groove 16A for allowing the first groove 6A to be communicated with the second groove 7A. Each of the third through fifth grooves 14A through 16A has a smaller cross-sectional area (flow passage area) than that of each of the first groove 6A, second groove 7a and external communication groove 8A, and has an elongated rectangular cross section perpendicular to the stream of the fluid (see FIGS. 1B through 1E). Each of the third through fifth grooves 14A through 16A is open on the side of the reverse 3 of the first member 2. Furthermore, as shown in FIG. 1A through 1E in this preferred embodiment, the first groove 6A, the second groove 7A and the external communication groove 8A substantially have the same cross-sectional area (see FIGS. 1A through 1D), and the third through fifth grooves 14A through 16A substantially have the same cross-sectional area. However, the present invention should not be limited thereto. For example, the first groove 6A may have a different cross-sectional area from that of the second groove 7A. Alternatively, the external communication groove 8A may have a different cross-sectional area from that of the first groove 6A or second groove 7A, or the third and fourth grooves 14A and 15A may be communicated with the outside without providing the external communication groove 8A.

If the second member 4 is piled on the reverse 3 of the first member 2 to close the openings of the first through fifth grooves 6A 7A, 14A through 16A and external communication groove 8A on the side of the reverse 3 of the first member 2, the first flow passage 6 and second flow passage 7 communicated with each other via the connecting portion 10 are formed, and the external environment communication passage 8 communicated with the first flow passage 6 and second flow passage 7 via the connecting portion 10 is formed. In addition, if the second member 4 is piled on the reverse 3 of the first member 2 to close the openings of the third through fifth grooves 14A through 16A of the connecting portion 10 on the side of the reverse 3 of the first member 2, the third flow passage 14 for allowing the first flow passage 6 to be communicated with the external environment communication passage 8, the fourth flow passage 15 for allowing the second flow passage 7 to be communicated with the external environment communication passage 8, and the fifth flow passage 16 for allowing the first flow passage 6 to be communicated with the second flow passage 7 are formed.

Each of the first through fifth flow passages 6, 7, 14 through 16 is formed so as to have such a flow passage area (cross-sectional area) and flow passage surface properties that a liquid can move in the flow passage due to capillarity (for example, the flow passage is formed so that the flow passage surface properties are lyophilic in view of an affinity between the flow passage and a liquid if the surface tension of the liquid is large).

As shown in FIG. 1A, the first flow passage 6 is designed to have a first port 17 for feeding a first liquid into the flow passage, or to be connected to a flow passage (not shown) for feeding a first liquid into the flow passage. The second flow passage 7 is designed to have a second port 18 for feeding a second liquid into the flow passage, or to be connected to a flow passage (not shown) for feeding a second liquid into the flow passage. The external environment communication passage 8 is designed to allow the first flow passage 6 and second flow passage 7 to be communicated with the outside environment.

In the flow handling apparatus 1 with the above described construction, if a first liquid is fed into the first flow passage 6 from the first port 17, the first liquid moves toward the connecting portion 10 in the first flow passage 6 due to capillarity. At this time, gas in the first flow passage 6 is pushed by the first liquid, which moves in the first flow passage 6 due to capillarity, to be exhausted to the external environment via the third flow passage 14 and external environment communication passage 8, or to be exhausted to the external environment via the fifth flow passage 15, second flow passage 7, fourth flow passage 15 and external environment communication passage 8. As a result, the first liquid moving in the first flow passage 6 due to capillarity reaches the end of the first flow passage 6 on the side of the connecting portion 10, and then, reaches the end of the third flow passage 14 on the side of the external environment communication passage 8 and the end of the fifth flow passage 16 on the side of the second flow passage 7 due to capillarity. When the first liquid reaches the end of the third flow passage 14 on the side of the external environment communication passage 8, the movement of the first liquid due to capillarity is stopped at the open end of the third flow passage 14 on the side of the external environment communication passage 8 so that the first liquid is not discharged to the external environment communication passage 8, since the flow passage area of the third flow passage 14 is abruptly increased to that of the external environment communication passage 8. When the first liquid reaches the end of the fifth flow passage 16 on the side of the second flow passage 7, the movement of the first liquid due to capillarity is stopped at the open end of the fifth flow passage 16 on the side of the second flow passage 7 so that the first liquid is not discharged to the second flow passage 7, since the flow passage area of the fifth flow passage 16 is abruptly increased to that of the second flow passage 7.

Then, if a second liquid is fed into the second flow passage 7 from the second port 18, the second liquid moves toward the connecting portion 10 in the second flow passage 6 due to capillarity. At this time, gas in the second flow passage 7 is pushed by the second liquid, which moves in the second flow passage 7 due to capillarity, to be exhausted to the external environment via the fourth flow passage 15 and external environment communication passage 8. As a result, the second liquid moving in the second flow passage 7 due to capillarity reaches the end of the second flow passage 7 on the side of the connecting portion 10, and then, reaches the end of the fourth flow passage 15 on the side of the external environment communication passage 8 due to capillarity. Then, the second liquid reaching the end of the second flow passage 7 on the side of the connecting portion 10 is associated with the first liquid, which is arranged at the end of the fifth flow passage 16 on the side of the second flow passage 7 (in the connecting portion 10), for forming a liquid-liquid interface level. In this case, if one of the first and second liquids is a protein solution and the other is a liquid reagent, the protein solution is mixed with the reagent via the liquid-liquid interface level, so that the crystallization of the protein is promoted by the moving boundary diffusion method (or carrier-free diffusion method) via the liquid-liquid interface level. Furthermore, when the second liquid reaches the end of the fourth flow passage 15 on the side of the external environment communication passage 8 due to capillarity, the movement of the second liquid due to capillarity is stopped at the open end of the fourth flow passage 15 on the side of the external environment communication passage 8 so that the second liquid is not discharged to the external environment communication passage 8, since the flow passage area of the fourth flow passage 15 is abruptly increased to that of the external environment communication passage 8.

According to the fluid handling apparatus 1 with such a construction, it is possible to easily form a liquid-liquid interface level by the movement of the first and second liquids due to capillarity, so that it is not required to provide any valve structure which is opened and closed by pressure. Therefore, it is possible to simplify the structure of the apparatus, and it is possible to miniaturize the whole structure of the apparatus.

Furthermore, if a second liquid reaches the connecting portion 10 prior to the arrival of a first liquid by feeding the first liquid into the first flow passage 6 after the second liquid is fed into the second flow passage 7, a liquid-liquid interface level between the first liquid and the second liquid is formed on the interface between the fifth flow passage 16 (the connecting portion 10) and the first flow passage 6.

Figure 7:
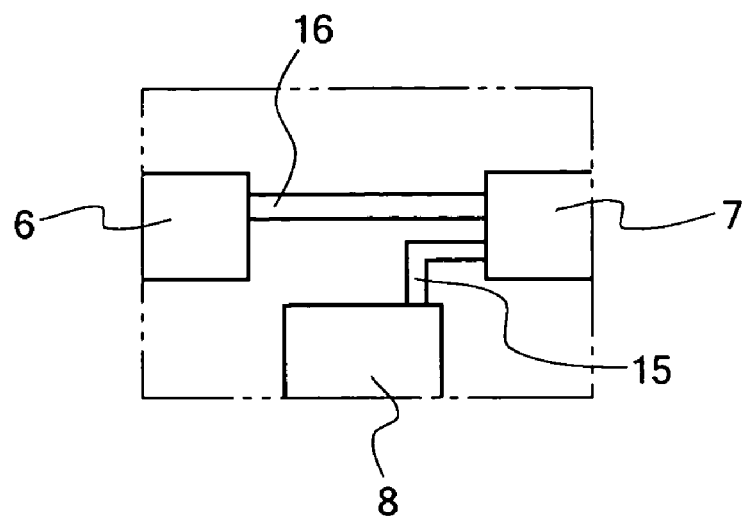
FIG. 7 is a plan view showing a connecting portion and flow passages in the vicinity thereof as a modified example of a part of the fluid handling apparatus in the first preferred embodiment.

If the first and second fluids are thus sequentially fed into the connecting portion 10, one of the flow passage for allowing the first flow passage to be communicated with the external environment, and the flow passage for allowing the second flow passage to be communicated with the external environment may be omitted. For example, if a second fluid is fed into the second flow passage 7 after a first fluid is fed into the first flow passage 6 to reach the connecting portion 10, even if the third flow passage 14 is not formed, the first fluid causes gas in the first flow passage 6 to be pushed into the second flow passage 7 via the fifth flow passage 16, and gas in the second flow passage 7 can be exhausted to the external environment via the fourth flow passage 15 when the second fluid is fed into the second flow passage 7 (see FIG. 7).

Second Preferred Embodiment

FIGS. 3A through 3E, 4A and 4B show the second preferred embodiment of a fluid handling apparatus 1 according to the present invention. Since the fluid handling apparatus 1 in this preferred embodiment has the same basic structure as that of the fluid handling apparatus 1 in the first preferred embodiment except for the flow passage structure of the connecting portion 10, the same reference numbers are given to the same structural portions as those of the fluid handling apparatus 1 in the first preferred embodiment to omit the duplicate descriptions thereof.

Figure 3A:
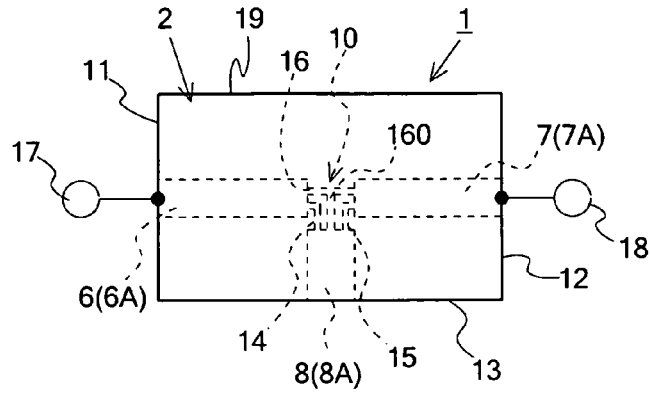
Figure 3C:
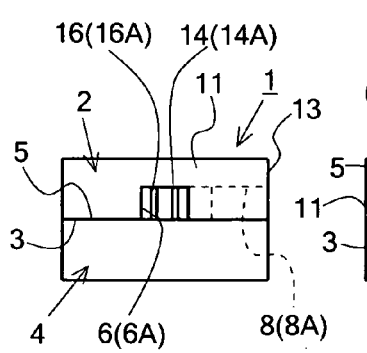
Figure 3B:
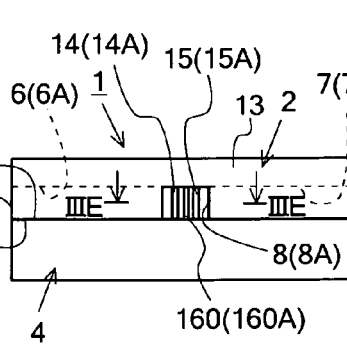
Figure 3D:
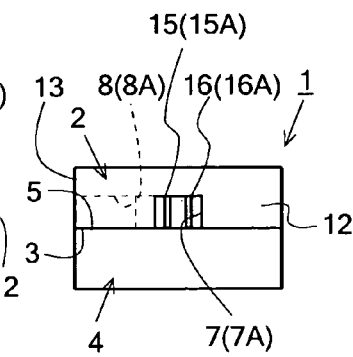
Figure 3E:
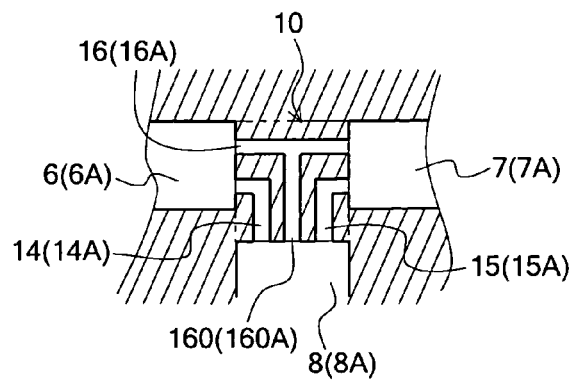
Figure 4A:
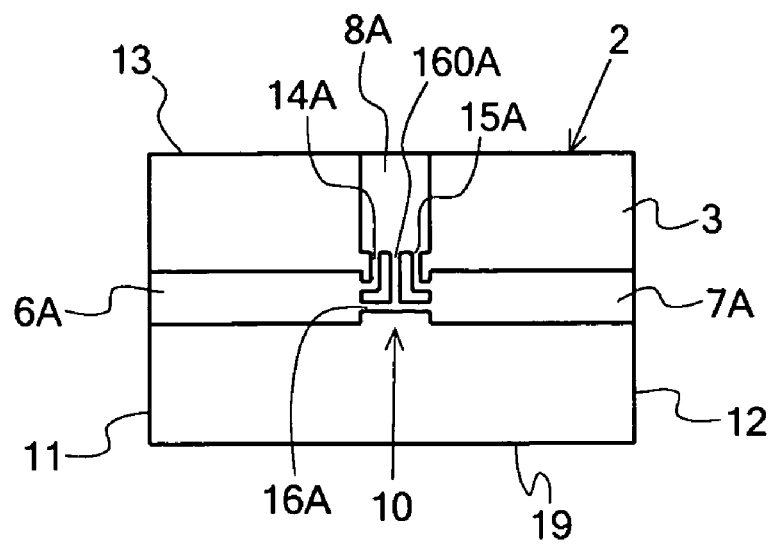
FIG. 4A is a bottom view of a first member of the fluid handling apparatus of FIGS. 3A through 3E.
Figure 4B:
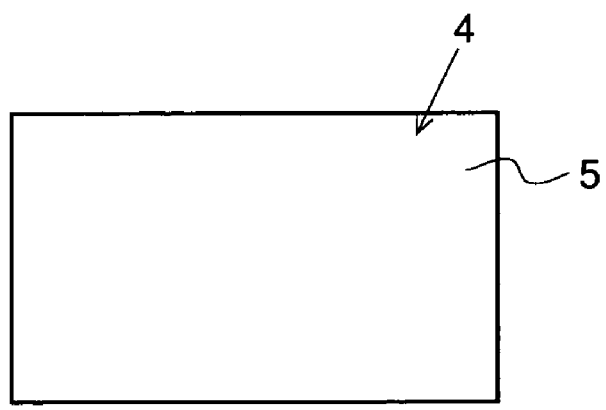
FIG. 4B is a plan view of a second member of the apparatus.

In this preferred embodiment, as shown in FIG. 3E, the fifth flow passage 16 of the connecting portion 10 has a branching passage portion 160 which branches off from a linear portion allowing the first flow passage 6 to be communicated with the second flow passage 7. Thus, the fifth flow passage 16 allows the first flow passage 6, the second flow passage 7 and the external environment communication passage 8 to be communicated with each other. As shown in FIG. 4A, the branching passage portion 160 of the fifth flow passage 16 is formed by closing a branching groove portion 160A, which is formed in the reverse 3 of the first member 2 so as to allow the linear portion of the fifth groove 16A to be communicated with the external communication groove 8A, with the second member 4. The flow passage cross-sectional shape of the branching passage portion 160 is substantially the same rectangle as that of the fifth flow passage 16 expect for the branching passage portion 160 (as that of the linear portion of the fifth flow passage 16).

In the fluid handling apparatus 1 in this preferred embodiment, if the first liquid fed into the first flow passage 6 and the second fluid fed into the second flow passage 7 simultaneously reach the connecting portion 10, gas arranged between the first and second liquids flowing in the fifth flow passage 16 due to capillarity can be exhausted to the external environment via the branching passage portion 160 and external environment communication passage 8, so that a liquid-liquid interface level between the first liquid and the second liquid can be formed in the fifth flow passage 16 (in the connecting portion 10).

In the fluid handling apparatus 1 in this preferred embodiment, if there is a difference in arrival time at the connecting portion 10 between the first liquid fed into the first flow passage 6 and the second liquid fed into the second flow passage 7, a liquid-liquid interface level between the first liquid and the second liquid is formed at the end of the fifth flow passage 16 on the side of the first flow passage 6 or at the end of the fifth flow passage 16 on the side of the second flow passage 7, similar to the above described first preferred embodiment.

Third Preferred Embodiment

FIGS. 5A through 5E, 6A and 6B show the third preferred embodiment of a fluid handling apparatus 1 according to the present invention. Since the fluid handling apparatus 1 in this preferred embodiment has the same basic structure as that of the fluid handling apparatus 1 in the first preferred embodiment except for the flow passage structure of the connecting portion 10, the same reference numbers are given to the same structural portions as those of the fluid handling apparatus 1 in the first preferred embodiment to omit the duplicate descriptions thereof.

Figure 5A:
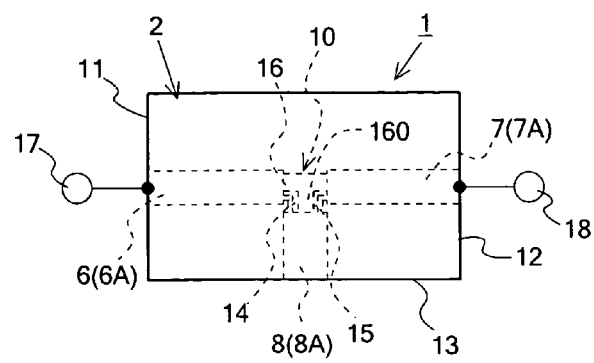
Figures 5B, 5C, 5D:
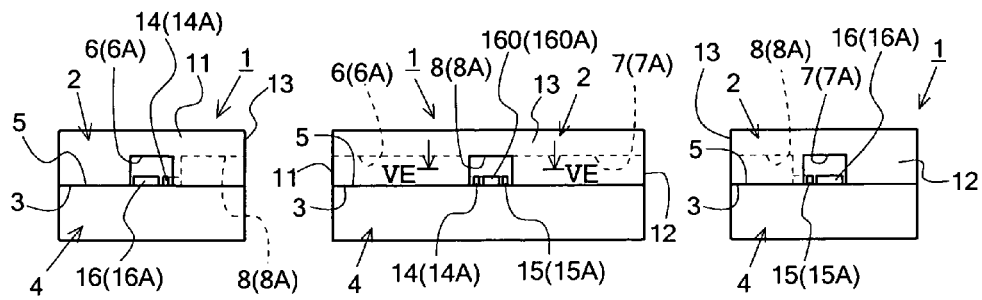
Figure 5E:
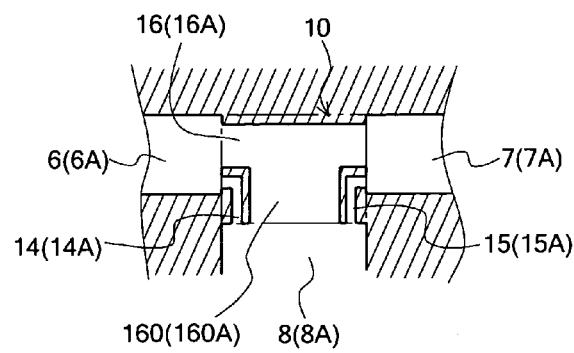
Figure 6A:
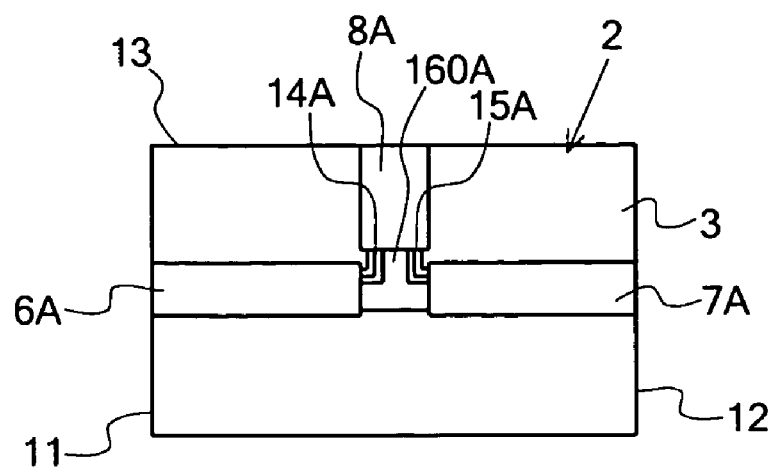
FIG. 6A is a bottom view of a first member of the fluid handling apparatus of FIGS. 5A through 5E.
Figure 6B:
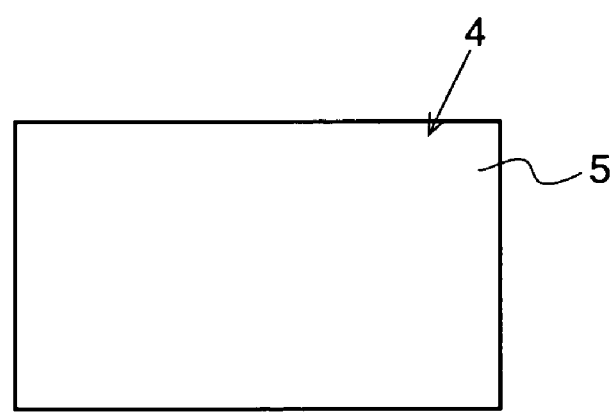
FIG. 6B is a plan view of a second member of the apparatus.

In this preferred embodiment as shown in FIGS. 5B through 5D, the depth of each of the third groove 14A, fourth groove 15A and fifth groove 16A (including the branching groove portion 160A) in the connecting portion 10 is smaller than the depth of each of the first groove 6A, second groove 7A and external communication groove 8A. Thus, even if the width of the fifth groove 16A (including the branching groove portion 160A) is greater than the width of the fifth groove 16A in the second preferred embodiment (see FIGS. 5E and 6A), the flow passage area of each of the third flow passage 14, fourth flow passage 15 and fifth flow passage 16 can be smaller than the flow passage area of each of the first flow passage 6, second flow passage 7 and external environment communication passage 8, so that it is possible to fulfill the same function as that of the connecting portion 10 in the second preferred embodiment. Therefore, the fluid handling apparatus 1 in this preferred embodiment can obtain the same advantageous effects as those of the fluid handling apparatus 1 in the second preferred embodiment.

When the first member 2 is formed by the injection molding, if the aspect ratio of the fifth groove 16A is large, i.e., if the depth of the fifth groove 16A is greater than the width thereof, it is difficult to transfer the shape of the bottom of the groove, so that it is difficult to obtain a desired shape of the fifth groove 16A. On the other hand, the connecting portion 10 in this preferred embodiment substantially has the same cross-sectional area as that in the second preferred embodiment by decreasing the aspect ratio of the fifth groove 16A, i.e., by increasing the width of the fifth groove 16A with respect to the depth thereof. Thus, the fifth groove 16A having a desired shape capable of obtaining the same advantageous effects as those in the second preferred embodiment can be easily formed by the injection molding.

The present invention should not be limited to the above described first through third preferred embodiments wherein the first through fifth grooves 6A, 7A, 14A, 15A, 16A (160A) and the external communication groove 8A are formed in the reverse 3 of the first member 2. The first through fifth grooves 6A, 7A, 14A, 15A, 16A (160A) and the external communication groove 8A may be divided between the reverse 3 of the first member 2 and the surface 5 of the second member 4 to be formed therein, and the surface 5 of the second member 4 may be caused to closely contact the reverse 3 of the first member 2 to form the first through fifth flow passages 6, 7, 14, 15, 16 and the external environment communication passage 8. Alternatively, the first through fifth grooves 6A, 7A, 14A, 15A, 16A (160A) and the external communication groove 8A may be formed in the reverse 3 of the first member 2 and the surface 5 of the second member 4 so as to extend in both of the first member 2 and the second member 4, and the reverse 3 of the first member 2 may be arranged so as to face the surface 5 of the second member 4 to form the first through fifth flow passages 6, 7, 14, 15, 16 and external environment communication passage 8 which extend in both of the first member 2 and the second member 4.

Figure 8:
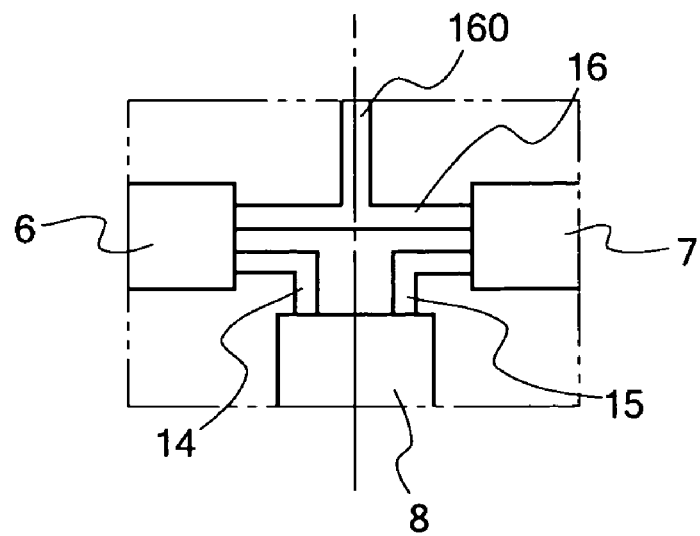
FIG. 8 is a plan view showing a connecting portion and flow passages in the vicinity thereof as a first example of a part of another preferred embodiment of a fluid handling apparatus according to the present invention.
Figure 9:
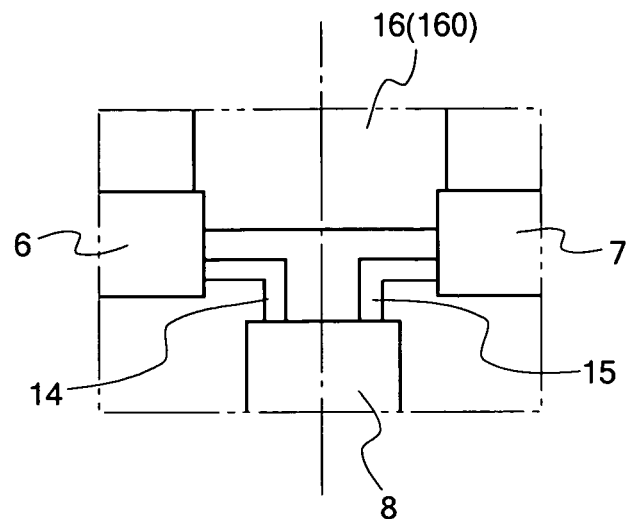
FIG. 9 is a plan view showing a connecting portion and flow passages in the vicinity thereof as a second example of a part of another preferred embodiment of a fluid handling apparatus according to the present invention.
Figure 10:
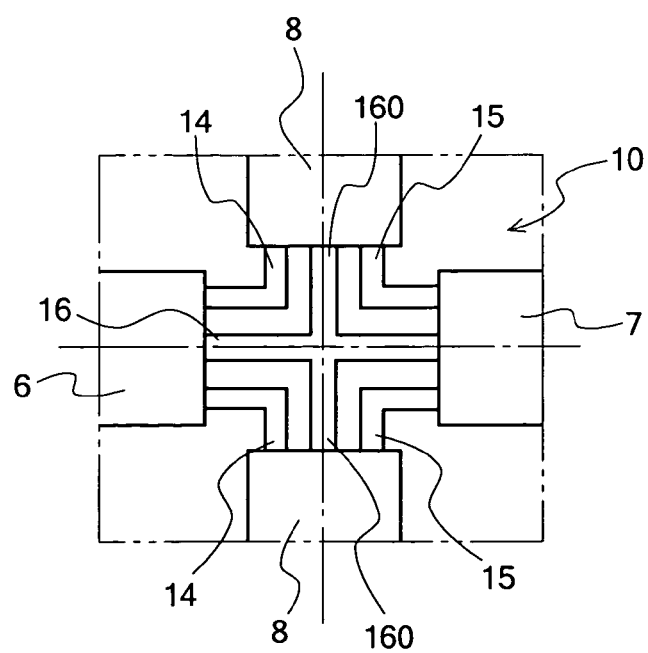
FIG. 10 is a plan view showing a connecting portion and flow passages in the vicinity thereof as a third example of a part of another preferred embodiment of a fluid handling apparatus according to the present invention.

Furthermore, the branching passage portion 160 of the fifth flow passage 16 shown in FIG. 3E may be open toward the opposite side surface 19 to the front side surface 13 of the first member 2 (see FIG. 8). If the communication with the external environment is thus divided between the side of the front side 13 and the side of the side surface 19, each of the third through fifth flow passages having a small cross-sectional area can be a flow passage having a small aspect ratio, so that it is possible to easily produce the first member 2 by the injection molding. In this case, if the width of the branching passage portion 160 is substantially equal to the length of the fifth flow passage 16 (in the direction of the stream of the fluid) (see FIG. 9), it is possible to more surely exhaust gas to the external environment when the first fluid and the second fluid are simultaneously fed into the first passage 6 and the second passage 7, respectively. Alternatively, the third flow passage 14, fourth flow passage 15 and branching passage portion 160 shown in FIG. 3E may be formed so as to be symmetrical with respect to the fifth flow passage 16 (see FIG. 10). If a plurality of flow passages communicated with the external environment are thus formed, it is possible to more surely exhaust gas to the external environment.

Fourth Preferred Embodiment

Figure 11A:
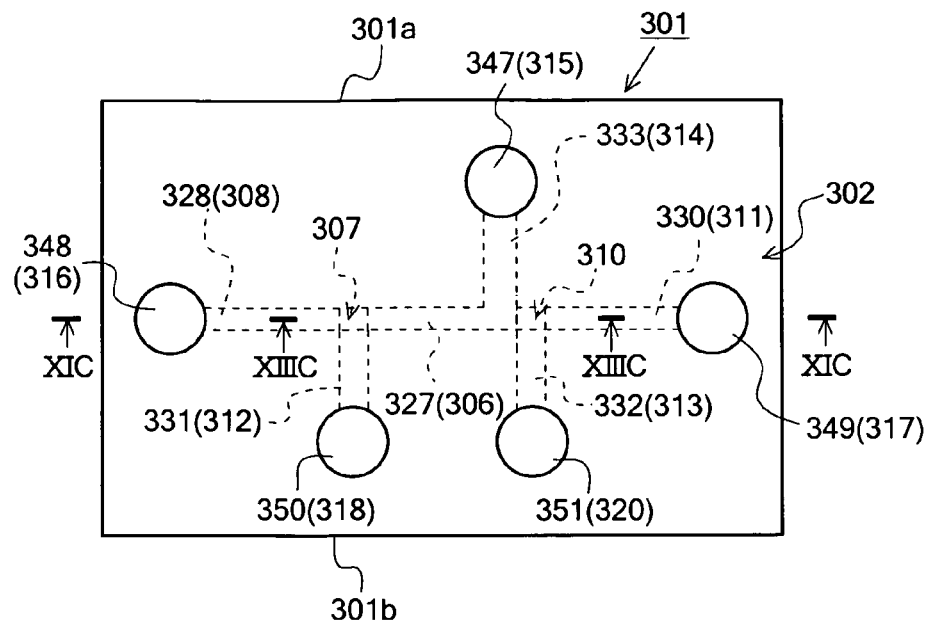
Figure 11B:
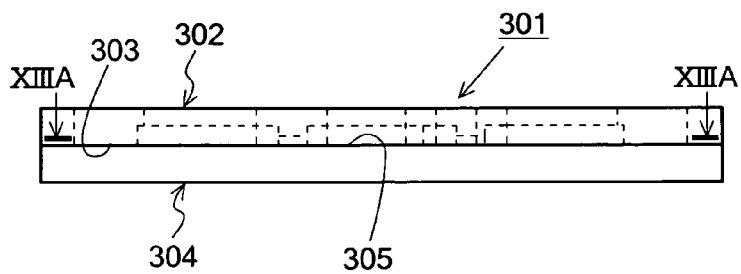
Figure 11C:
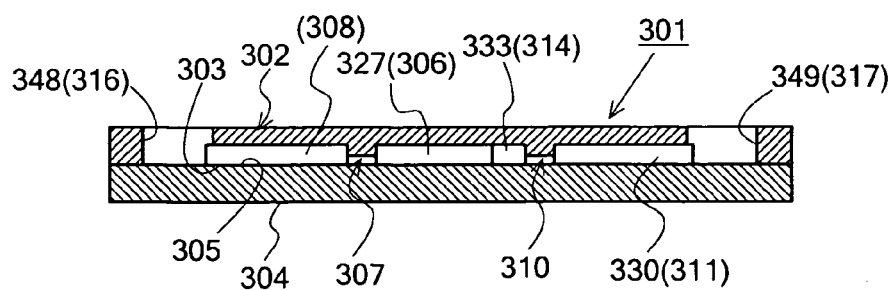

FIGS. 11A through 11C show the fourth preferred embodiment of a fluid handling apparatus 1 according to the present invention. FIG. 11A is a plan view of the fluid handling apparatus 301, and FIG. 11B is a side view of the fluid handling apparatus 301. FIG. 11C is a sectional view taken along line XIC-XIC in FIG. 11A. As shown in FIGS. 11A through 11C, the fluid handling apparatus 301 in this preferred embodiment comprises a first sheet-like member 302 having a rectangular planar shape, and a second sheet-like member 304 arranged so as to cover the whole reverse 303 of the first member 302. The first member 302 and the second member 304 are made of any one of various resin materials, such as polymethyl methacrylate (PMMA) polycarbonate (PC) and ultraviolet curable resins, glasses and ceramics. The piled surfaces (facing surfaces) of the first and second members 302 and 304 (the reverse 303 of the first member 302 and the surface 305 of the second member 304 (see FIGS. 12A and 12B)) are smoothed flat surfaces having a good adhesion. The first member 302 is piled on the second member 304 so that the reverse 303 of the first member 302 closely contacts the surface 305 of the second member 304. In this state, the first member 302 is detachably or undetachably fixed to the second member 304 by means of an adhesion, fasteners, clips or the like. Furthermore, while the first member 302 and the second member 304 have been sheet-like members in this preferred embodiment, the present invention should not be limited thereto, but they may be cubic block-shaped members. Alternatively, the second member 304 to be piled on the reverse 303 of the first member 302 may be a film-like member.

Figure 12A:
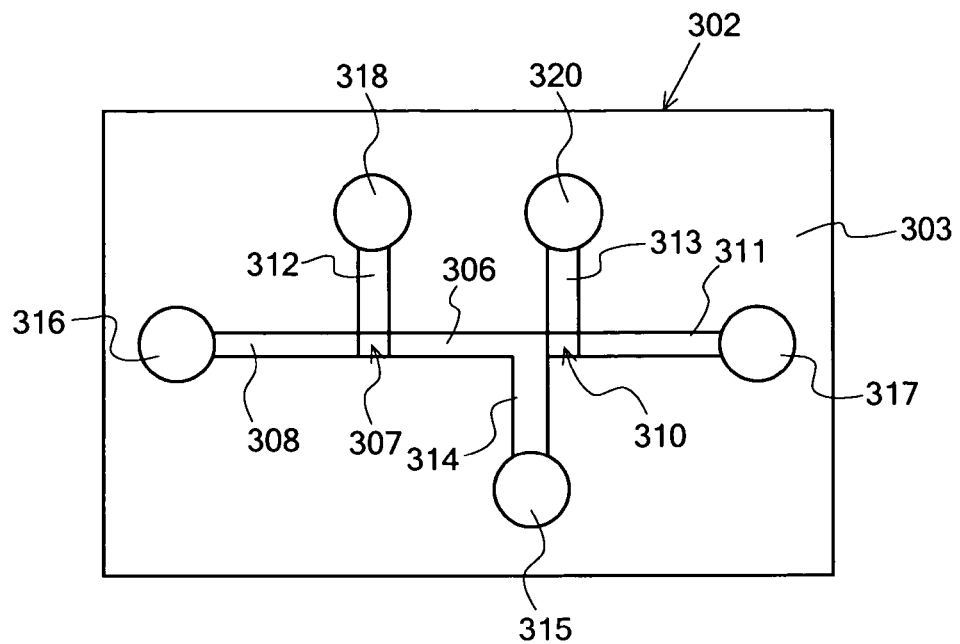
FIG. 12A is a bottom view of a first member of the fluid handling apparatus of FIGS. 11A through 11C.
Figure 12B:
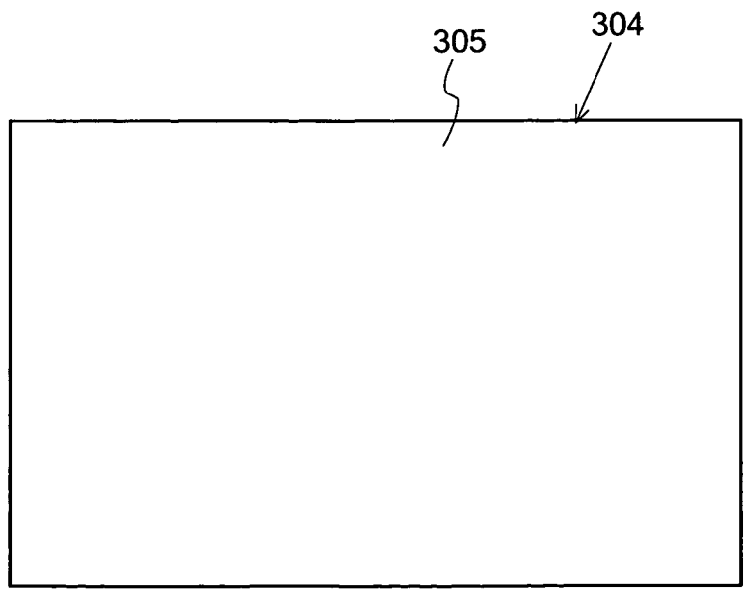
FIG. 12B is a plan view of a second member of the apparatus.
Figure 13A:
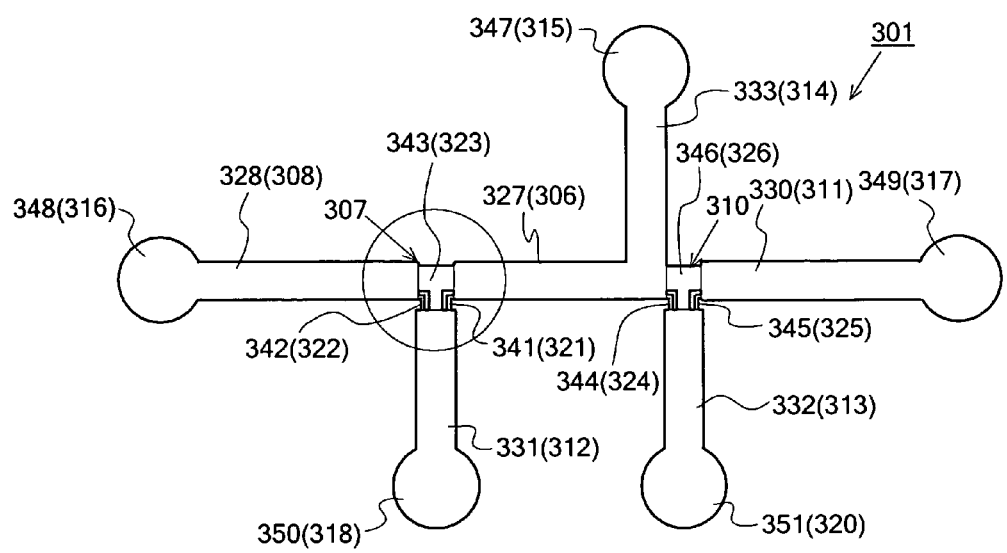
FIG. 13A is a sectional view taken along line XIIIA-XIIIA in FIG. 11B.
Figure 13B:
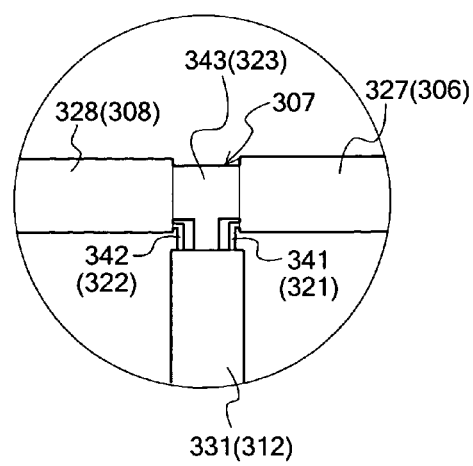
FIG. 13B is an enlarged view showing a region surrounded by a circle in FIG. 13A, FIG. 13C being a sectional view taken along line XIIIC-XIIIC in FIG. 11A, and FIG. 13D being an enlarged sectional view showing a region surrounded by a circle in FIG. 13C.
Figure 13C:
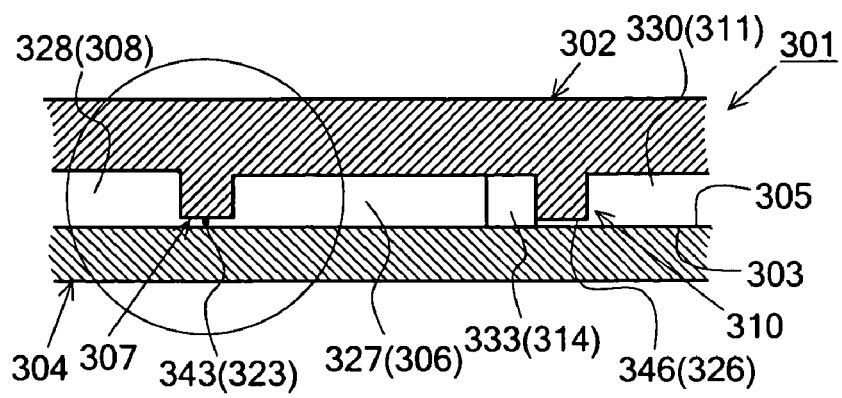
Figure 13D:
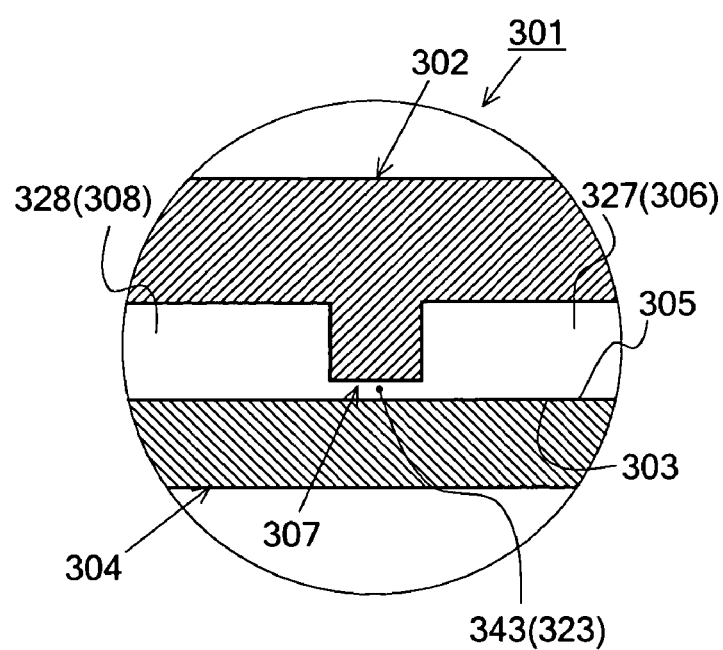
Figure 14A:
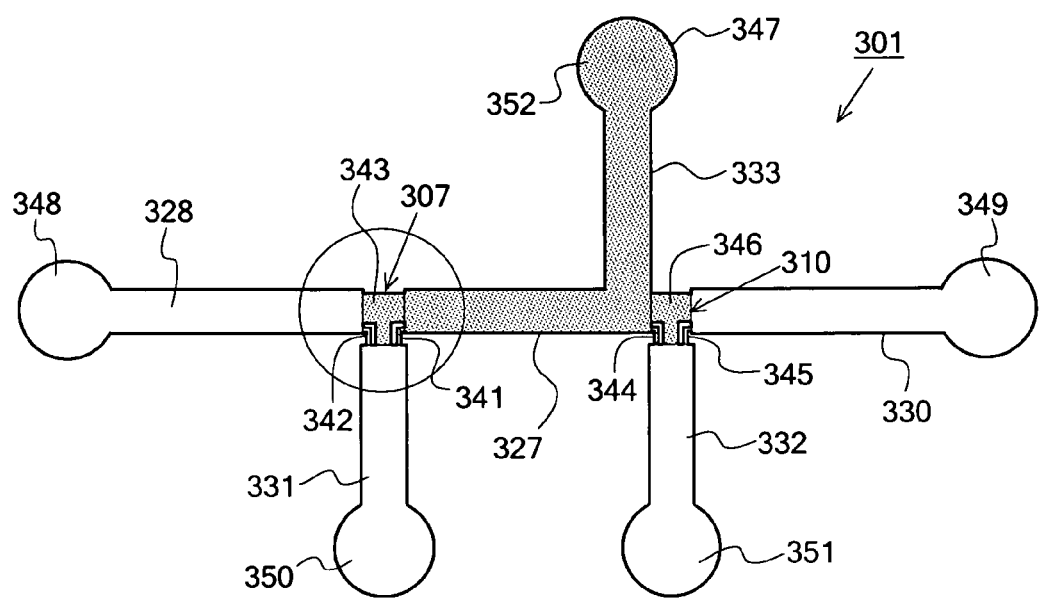
FIGS. 14A through 14D show a first operating state of the fourth preferred embodiment of a fluid handling apparatus according to the present invention, which correspond to FIGS. 13A through 13D.
Figure 14B:
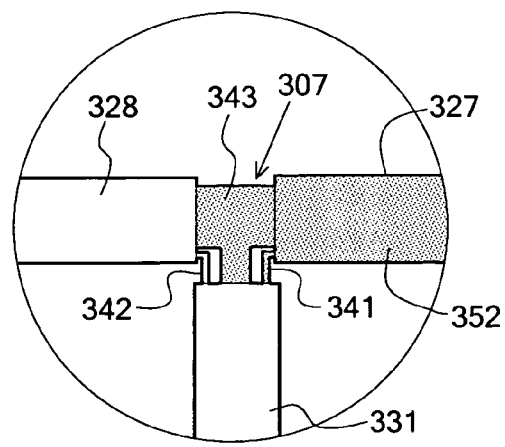
Figure 14C:
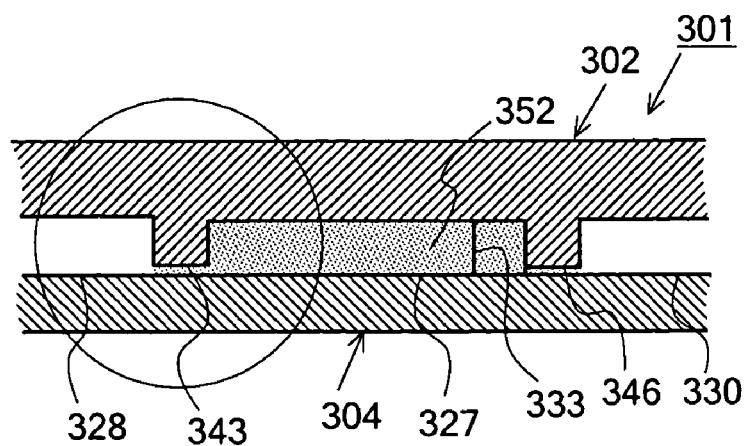
Figure 14D:
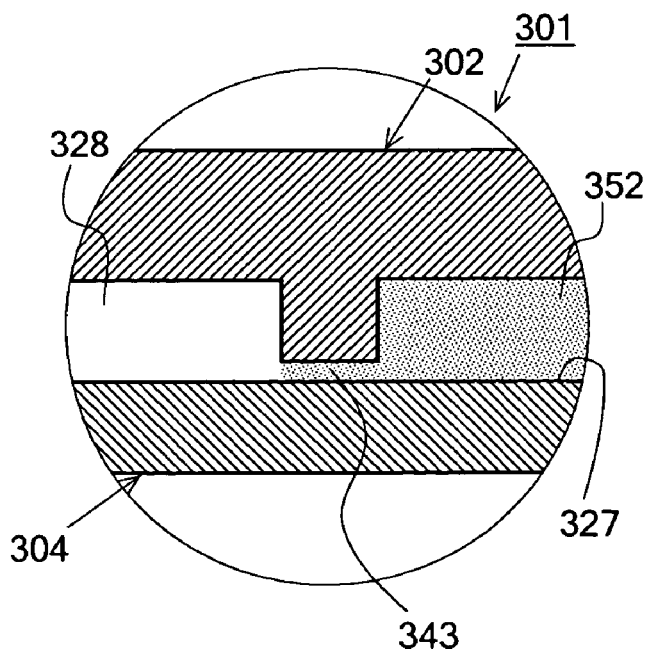

FIG. 12A is a bottom view of the first member 302. As shown in FIG. 12A, a first groove 306 linearly extending in lateral directions on the side of the reverse 303 of the first member, a second groove 308 communicated with one end of the first groove 306 via a first connecting portion 307, a third groove 311 communicated with the other end of the first groove 306 via a second connecting portion 310, a first external environment communication groove 312 communicated with the first groove 306 and second groove 308 via the first connecting portion 307, a second external environment communication groove 313 communicated with the first groove 306 and third groove 311 via the second connecting portion 310, and a sample feeding groove 314 communicated with the first groove 306 are formed in the reverse 303 of the first member 302. Each of the first groove 306, the second groove 308, the third groove 311, the first and second external environment communication grooves 312, 313 and the sample feeding groove 314 has a rectangular cross section, and is open on the side of the reverse 303 of the first member 302. The end of the sample feeding groove 314 has a hole 315 which passes through the first member 302 from the surface to reverse thereof. The ends of the second groove 308, third groove 311, and first and second external environment communication grooves 312, 313 have holes 316, 317, 318, 320, respectively, which pass through the first member 302 from the surface to reverse thereof.

FIGS. 13A through 13D show the details of the first connecting portion 307 and second connecting portion 310. As shown in FIGS. 13A through 13D, the first connecting portion 307 has a first sub-groove 321, a second sub-groove 322 and a third sub-groove 323, each of which has a smaller cross-sectional area than that of each of the first groove 306, second groove 308 and first external environment communication groove 312. The first sub-groove 321 is designed to allow the first groove 306 to be communicated with the first external environment communication groove 312. The second sub-groove 322 is designed to allow the second groove 308 to be communicated with the first external environment communication groove 312. The third sub-groove 323 is designed to allow the first groove 306, the second groove 308 and the first external environment communication groove 312 to be communicated with each other. The second connecting portion 310 has a fourth sub-groove 324, a fifth sub-groove 325 and a sixth sub-groove 326, each of which has a smaller cross-sectional area than that of each of the first groove 306, third groove 311 and second external environment communication groove 313. The fourth sub-groove 324 is designed to allow the first groove 306 to be communicated with the second external environment communication groove 313. The fifth sub-groove 325 is designed to allow the third groove 311 to be communicated with the second external environment communication groove 313. The sixth sub-groove 326 is designed to allow the first groove 306, the third groove 311 and the second external environment communication groove 313 to be communicated with each other. Each of the first through sixth sub-grooves 321 through 326 has a rectangular cross-section, and is open on the side of the reverse 303 of the first member 302.

As shown in FIGS. 11A through 11C and FIG. 13A through 13D, if the second member 304 is piled on the reverse 303 of the first member 302 with the above described construction to close the openings of the first groove 306, second groove 308, third groove 311, first and second external environment communication groove 312, 313, sample feeding groove 314, first through sixth sub-grooves 321 through 326 and holes 315 through 318 and 320 by the second member 304, there are formed a first main flow passage 327, a second main flow passage 328, a third main flow passage 330, first and second external environment communication passage 331, 332, a sample feeding passage 333, first through sixth sub-flow passages 341 through 346, first through third ports 347 through 349, and first and second external environment communication ports 350, 351.

That is, as shown in FIGS. 13A through 13D, the first main flow passage 327 is communicated with the second main flow passage 328 via the first connecting portion 307, and is communicated with the third main flow passage 330 via the second connecting portion 310. In addition, the first main flow passage 327 is communicated with the first external environment communication passage 331 via the first connecting portion 307, and is communicated with the second external environment communication passage 332 via the second connecting portion 310.

As shown in FIGS. 13A through 13D, in the first connecting portion 307, the first sub-flow passage 341 allows the first main flow passage 327 to be communicated with the first external environment communication passage 331, and the second sub-flow passage 342 allows the second main flow passage 328 to be communicated with the first external environment communication passage 331. In addition, the third sub-flow passage 343 allows the first main flow passage 327, the second main flow passage 328 and the first external environment communication passage 331 to be communicated with each other.

As shown in FIGS. 13A through 13D, in the second connecting portion 310, the fourth sub-flow passage 344 allows the first main flow passage 327 to be communicated with the second external environment communication passage 332, and the fifth sub-flow passage 345 allows the third main flow passage 330 to be communicated with the second external environment communication passage 332. In addition, the sixth sub-flow passage 346 allows the first main flow passage 327, the third main flow passage 330 and the second external environment communication passage 332 to be communicated with each other.

Each of the above described first through third main flow passages 327, 328, 330, sample feeding passage 333 and first through sixth sub-flow passage 341 through 346 is formed so as to have such a cross-sectional area (flow passage area) and flow passage surface properties that a liquid fed into the interior of the flow passage can move in the flow passage due to capillarity (for example, the flow passage is formed so that the flow passage surface properties are lyophilic in view of an affinity between the flow passage and a liquid if the surface tension of the liquid is large).

As shown in FIGS. 14A through 14D, if a sample 352 containing an analyzing object serving as a first fluid (which will be hereinafter referred to as a "sample 352") is fed into the first port 347 of the fluid handling apparatus 301 with the above described construction, the sample 352 is fed into the first main flow passage 327 via the sample feeding passage 333 due to capillarity. At this time, gas in the first main flow passage 327 (including gas in the sample feeding passage 333) is pushed by the sample 352, which moves in the first main flow passage 327 due to capillarity, to be exhausted to the external environment via the first sub-flow passage 341 of the first connecting portion 307 and the first external environment communication passage 331, and to be exhausted to the external environment via the third sub-flow passage 343, second main flow passage 328, second sub-flow passage 342 and first external environment communication passage 331. In addition, the sample 352 moving in the sample feeding passage 333 pushes gas toward the second connecting portion 310, so that gas is exhausted to the external environment via the fourth sub-flow passage 344 and the second external environment communication passage 332, and is exhausted to the external environment via the sixth sub-flow passage 346, third main flow passage 330, fifth sub-flow passage 345 and second external environment communication passage 332.

As a result, as shown in FIGS. 14A through 14D, if the sample 352 moving in the first main flow passage 327 due to capillarity reaches the first connecting portion 307, the sample 352 moves in the first sub-flow passage 341 to the end of the first sub-flow passage 341 on the side of the first external environment communication passage 331 due to capillarity while pushing gas. In addition, the sample 352 moves in the third sub-flow passage 343 to the ends of the third sub-flow passage 343 on the side of the second main flow passage 328 and on the side of the external environment communication passage 331 due to capillarity while pushing gas. The sample 352 reaching the ends of the first sub-flow passage 341 and third sub-flow passage 343 on the side of the first external environment communication passage 331 due to capillarity is stopped at the open ends of the first sub-flow passage 341 and third sub-flow passage 343 on the side of the first external environment communication passage 331, since the flow passage area of each of the first sub-flow passage 341 and third sub-flow passage 343 is abruptly increased to that of the first external environment communication passage 331. In addition, the sample 352 reaching the end of the third sub-flow passage 343 on the side of the second main flow passage 328 due to capillarity is stopped at the open end of the third sub-flow passage 343 on the side of the second main flow passage 328, since the flow passage area of the third sub-flow passage 343 is abruptly increased to that of the second main flow passage 328.

As shown in FIG. 14A through 14D, if the sample 352 moving in the first main flow passage 327 due to capillarity reaches the second connecting portion 310, the sample 352 moves in the fourth sub-flow passage 344 to the end of the fourth sub-flow passage 344 on the side of the second external environment communication passage 332 due to capillarity while pushing gas. In addition, the sample 352 moves in the sixth sub-flow passage 346 to the ends of the sixth sub-flow passage 346 on the side of the third main flow passage 330 and on the side of the external environment communication passage 332 due to capillarity while pushing gas. The sample 352 reaching the ends of the fourth sub-flow passage 344 and sixth sub-flow passage 346 on the side of the second external environment communication passage 332 due to capillarity is stopped at the open ends of the fourth sub-flow passage 344 and sixth sub-flow passage 346 on the side of the second external environment communication passage 332, since the flow passage area of each of the fourth sub-flow passage 344 and sixth sub-flow passage 346 is abruptly increased to that of the second external environment communication passage 332. In addition, the sample 352 reaching the end of the sixth sub-flow passage 346 on the side of the third main flow passage 330 due to capillarity is stopped at the open end of the sixth sub-flow passage 346 on the side of the third main flow passage 330, since the flow passage area of the sixth sub-flow passage 346 is abruptly increased to that of the third main flow passage 330.

Then, as shown in FIGS. 15A through 15D, if polymer solutions (second and third fluids) 353 and 354 are injected from the second port 348 and third port 349, respectively, the polymer solution (second fluid) 353 injected from the second port 348 moves in the second main flow passage 328 due to capillarity, and the polymer solution (third fluid) 354 injected from the third port 349 moves in the third main flow passage 330 due to capillarity. At this time, the polymer solution 353 injected from the second port 348 exhausts gas to the external environment from the second sub-flow passage 342 via the first external environment communication passage 331 when it moves in the second main flow passage 328 due to capillarity. Then, the polymer solution 353 reaches the first connecting portion 307, so that a liquid-liquid interface level between the polymer solution 353 and the sample 352 is formed on the interface between the second main flow passage 328 and the third sub-flow passage 343, and the polymer solution 353 moves to the end of the second sub-flow passage 342 on the side of the first external environment communication passage 331 due to capillarity. The polymer solution 353 reaching the end of the second sub-flow passage 342 on the side of the first external environment communication passage 331 due to capillarity is stopped at the open end of the second sub-flow passage 342 on the side of the first external environment communication passage 331, since the flow passage area of the second sub-flow passage 342 is abruptly increased to that of the first external environment communication passage 331. In addition, the polymer solution 354 injected from the third port 349 exhausts gas to the external environment from the fifth sub-flow passage 345 via the second external environment communication passage 332 when it moves in the third main flow passage 330 due to capillarity. Then, the polymer solution 354 reaches the second connecting portion 310, so that a liquid-liquid interface level between the polymer solution 354 and the sample 352 is formed on the interface between the third main flow passage 330 and the sixth sub-flow passage 346, and the polymer solution 354 moves to the end of the fifth sub-flow passage 345 on the side of the second external environment communication passage 332 due to capillarity. The polymer solution 354 reaching the end of the fifth sub-flow passage 345 on the side of the second external environment communication passage 332 due to capillarity is stopped at the open end of the fifth sub-flow passage 345 on the side of the second external environment communication passage 332, since the flow passage area of the fifth sub-flow passage 345 is abruptly increased to that of the second external environment communication passage 332. Furthermore, while the external environment communication passages 331 and 332 have been formed in this preferred embodiment, one end portion of each of the first, second, fourth and fifth sub-flow passages 341, 342, 344 and 345 may be directly communicated with the external environment without providing the external environment communication passages 331 and 332.

As described above, according to this preferred embodiment, the sample 352 or the polymer solution 353, 354 can be filled in the first through third main flow passages 327, 328, 330 and first and second connecting portions 307, 310 while preventing gas from remaining therein, so that it is possible to surely form a liquid-liquid interface level in the first connecting portion 307 and second connecting portion 310 (see FIGS. 15A through 15D).

In the fluid handling apparatus 301 in this preferred embodiment, the volume of the first main flow passage 327 arranged between the first connecting portion 307 and the second connecting portion 310 is set to be a desired volume, so that the first main flow passage 327 serves as a metering flow passage portion for metering a desired amount of sample (see FIGS. 13A through 13D, 14A through 14D, 15A through 15D). Furthermore, V2 is far smaller than V1 (V1>>2·V2) assuming that the volume of the first main flow passage 327 serving as the metering flow passage portion is V1 and that each of the volume of the third sub-flow passage 343 in the first connecting portion 307 and the volume of the sixth sub-flow passage 346 in the second connecting portion 310 is V2. Therefore, the sample 352 is accurately metered by the first main flow passage 327.

Thereafter, electrodes (not shown) are arranged in the second port 348 of the second main flow passage 328, the third port 349 of the third main flow passage 330 and the first port 347 of the sample feeding passage 333, respectively. Then, a voltage is applied to the sample 352 in the first main flow passage 327 and sample feeding passage 333, the polymer solution 353 in the second main flow passage 328, and the polymer solution 354 in the third main flow passage 330, by a potential difference applying means, to move the analyzing objects of the sample 352 in the first main flow passage 327 and sample feeding passage 333 due to electrophoresis. As a result, various bands are produced since the moving speeds of the analyzing objects contained in the sample 352 in the first main flow passage 327 are different from each other due to differences in molecular weight and so forth. The bands thus produced can be moved toward the second main flow passage 328 via the first connecting portion 307 due to electrophoresis, to measure and analyze the analyzing objects by a sample measuring means (not shown) arranged in the second main flow passage 328. Alternatively, the bands thus produced can be moved toward the third main flow passage 330 via the second connecting portion 310 due to electrophoresis, to measure and analyze the analyzing objects by a sample measuring means (not shown) arranged in the third main flow passage 330. In addition, the analyzing objects of the sample 352 in the sample feeding passage 333 are returned toward the first port 347 due to electrophoresis (see FIGS. 15A through 15D).

Furthermore, when electrophoresis is thus carried out, the sample feeding passage 333 is preferably arranged at a position which is one end of the first main flow passage 327 for metering the sample 352 and which is an upstream position in directions of electrophoresis. If the sample feeding passage 333 is thus arranged, it is possible to prevent the analyzing objects in the sample 352 metered in the first main flow passage 327 from returning to the sample feeding passage 333 due to electrophoresis, so that it is possible to more accurately carry out quantitative analysis.

In the fluid handling apparatus 301 in this preferred embodiment with the above described construction, it is possible to feed the liquid sample 352 into the first main flow passage 327 via the sample feeding passage 333 due to capillarity, so that it is possible to simply meter a desired amount of sample 352 in the first main flow passage 327 arranged between the first connecting portion 307 and the second connecting portion 310.

In the fluid handling apparatus 301 in this preferred embodiment, it is possible to feed the liquid sample 352 into the first main flow passage 327 via the sample feeding passage 333 due to capillarity, and it is possible to feed the polymer solutions 353 and 354, which are used for moving the sample 352 due to electrophoresis, into the second main flow passages 328 and third main flow passage 330 from the second port 348 and third port 349 due to capillarity, respectively, so that it is possible to cause the polymer solutions 353 and 354 to contact the sample 352 in the first connecting portion 307 and second connecting portion 310, respectively, to form a liquid-liquid interface level. Therefore, it is not required to provide any vacuum equipment and pressurizing means, so that it is possible to simplify the structure of the apparatus and miniaturize the whole structure of the apparatus. In addition, it is not required to carry out a pretreatment by a vacuum equipment, and it is not required to pressurize the interior of the fluid passage at two stages by a pressurizing means, so that it is possible to remarkably shorten the time to analyze the sample 352.

In the fluid handling apparatus 301 in this preferred embodiment, gas in the first main flow passage 327 (including gas in the sample feeding passage 333) and gas in the second main flow passage 328 can be exhausted to the external environment via the first connecting portion 307, and gas in the first main flow passage 327 (including gas in the sample feeding passage 333) and gas in the third main flow passage 330 can be exhausted to the external environment via the second connecting portion 310. Therefore, it is possible to form a liquid-liquid interface level (an interface containing no gas) between the sample 352 and the polymer solution 352, 354, and it is possible to prevent gas from being mixed in the sample 352 and polymer solutions 353, 354, so that it is possible to smoothly and accurately analyze the sample 352 in the first main flow passage 327 due to electrophoresis.

In the fluid handling apparatus 301 in this preferred embodiment, if the sample 352 and the polymer solution 353 simultaneously reach the first connecting portion 307, gas in the third sub-flow passage 343 is pushed toward the first external environment communication passage 331 by the sample 352 and polymer solution 353 which are moved by capillarity, so that a liquid-liquid interface level between the sample 352 and the polymer solution 353 is formed in the third sub-flow passage 343. If the sample 352 and the polymer solution 354 simultaneously reach the second connecting portion 310, gas in the sixth sub-flow passage 346 is pushed toward the second external environment communication passage 332 by the sample 352 and polymer solution 354 which are moved by capillarity, so that a liquid-liquid interface level between the sample 352 and the polymer solution 354 is formed in the sixth sub-flow passage 346.

Figure 15A:
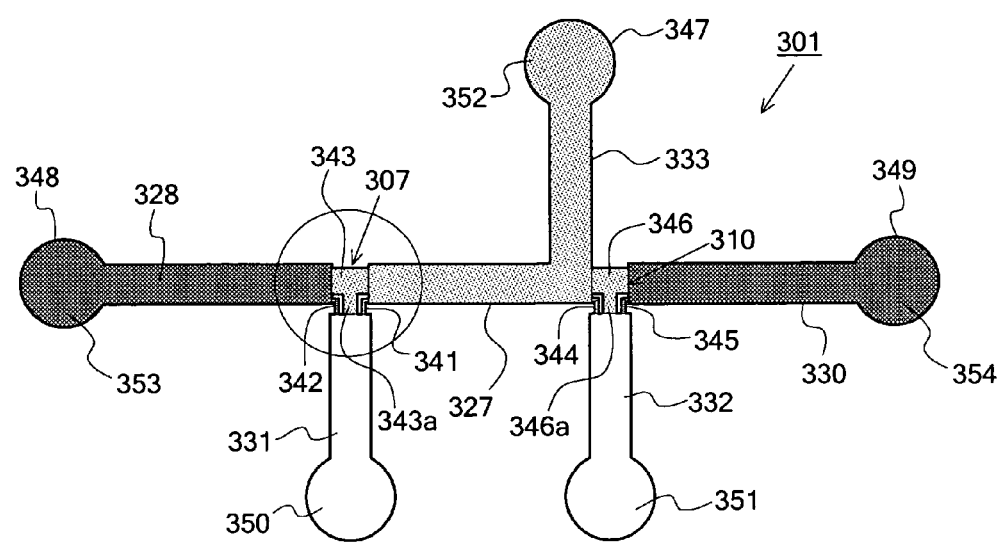
FIGS. 15A through 15E show a second operating state of the fourth preferred embodiment of a fluid handling apparatus according to the present invention, wherein FIGS. 15A through 15D correspond to FIGS. 13A through 13D.
Figure 15B:
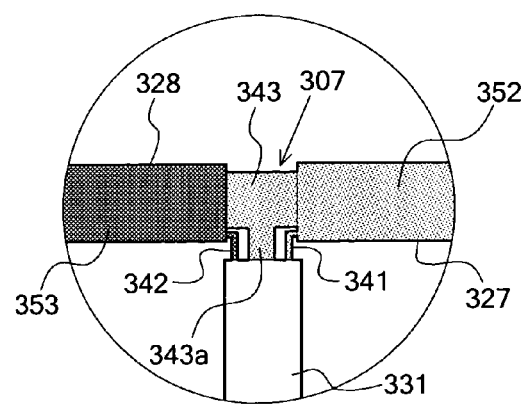
Figure 15C:
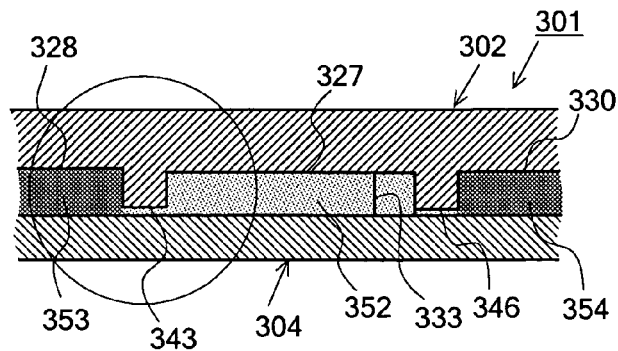
Figure 15D:
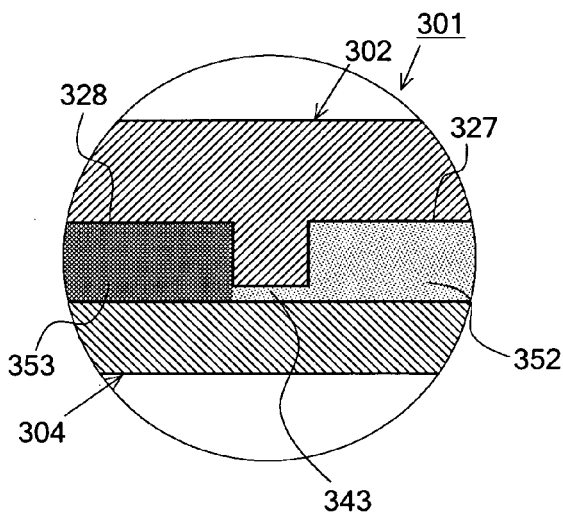
Figure 15E:
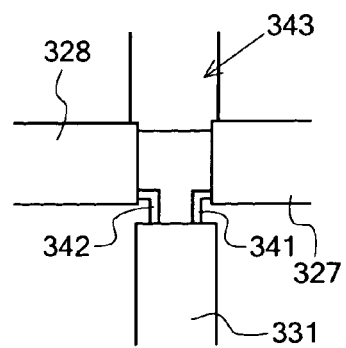
Figure 16A:
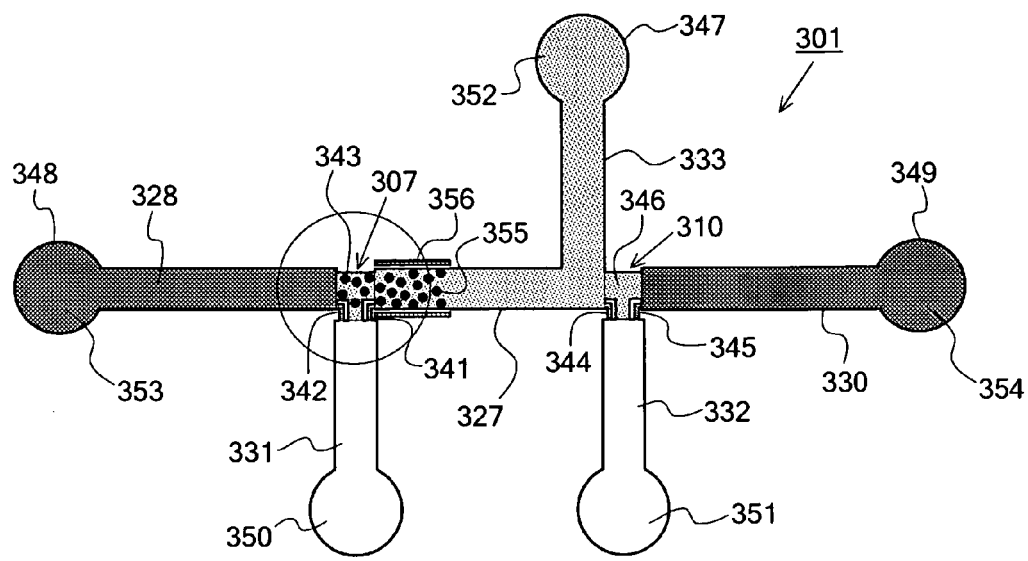
FIGS. 16A through 16D show the fifth preferred embodiment of a fluid handling apparatus according to the present invention, which correspond to FIGS. 15A through 15D.
Figure 16B:
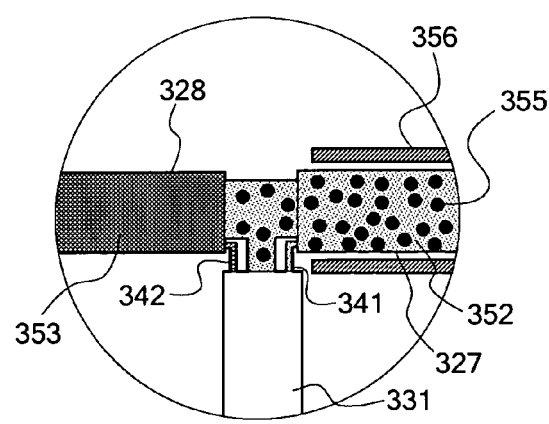
Figure 16C:
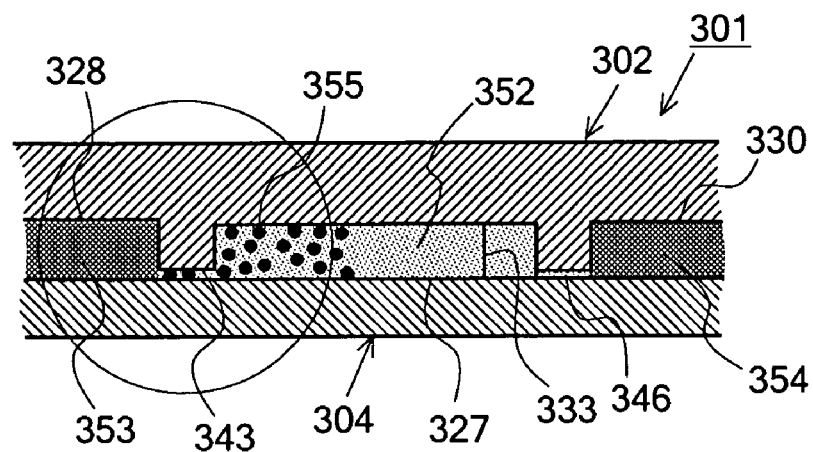
Figure 16D:
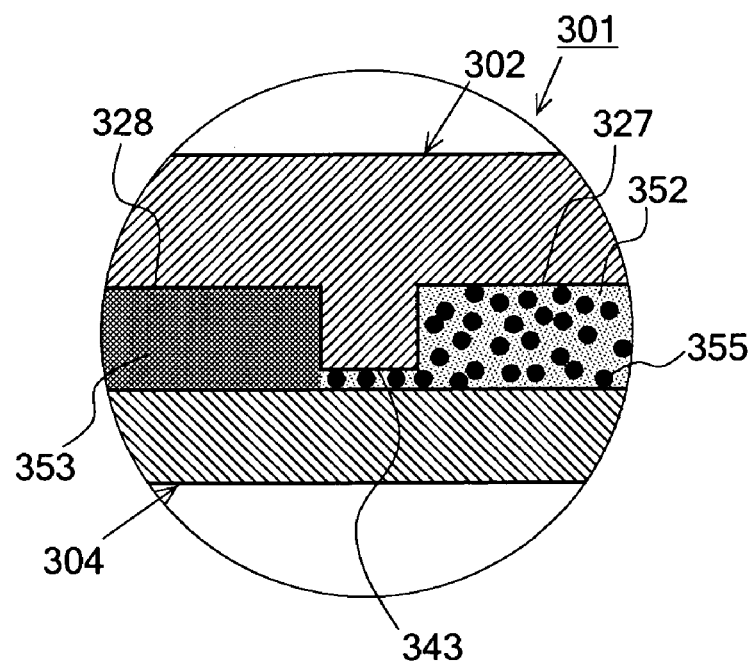

In order to more surely carry out such degassing, the width of the branching flow passage portion 343a of the third sub-flow passage 343 to the first external communication passage 331, and the width of the branching flow passage portion 346a of the sixth sub-flow passage 346 to the second external communication passage 332 may be increased so as to be substantially equal to the flow length of the third sub-flow passage 343 (the distance between the first main flow passage 327 and the second main flow passage 328) and to the flow length of the sixth sub-flow passage 346 (the distance between the first main flow passage 327 and the third main flow passage 330). Furthermore, if the branching flow passage portions 343a and 346a are formed on the opposite side surface 301a (see FIG. 11A) to the side surface 301b (see FIG. 11A) on the side of which the first and second sub-flow passages 341, 342 and the fourth and fifth sub-flow passages 344, 345 are formed, the width of each of the branching flow passage portions 343a and 346a can be equal to the flow length of each of the third sub-flow passage 343 and the sixth sub-flow passage 346 (see FIG. 15E).

If the width of each of the first through sixth sub-flow passages 341 through 346 in the first connecting portion 307 and second connecting portion 310 is decreased in thickness directions (if the depth of each of the first through sixth sub-grooves 321 through 326 is decreased) as this preferred embodiment, even if the width of each of the first through sixth sub-flow passages 341 through 346 in directions perpendicular to the thickness directions and the directions of the stream of the fluid is increased, the cross-sectional area of each of the first through sixth sub-flow passages 341 through 346 can be smaller than that of each of the first through third main flow passages 327, 328, 330 and the first and second external environment communication passages 331, 332, so that it is possible to surely exhaust gas in the flow passages.

If the aspect ratio of each of the first through sixth sub-grooves 321 through 326 for forming the first through sixth sub-flow passages 341 through 346 is large, i.e., if the depth of each of the first through sixth sub-grooves 321 through 326 is larger than the width thereof, it is difficult to transfer the shape of the bottom of each of the grooves by the injection molding, so that it is difficult to obtain a desired shape with respect to the grooves. On the other hand, if the aspect ratio of each of the first through sixth sub-grooves 321 through 326 is decreased as this preferred embodiment, i.e., if each of the first through sixth sub-grooves 321 through 326 is formed so as to have a desired cross-section by increasing the width thereof with respect to the depth thereof, the first through sixth sub-grooves 321 through 326 can be easily formed by the injection molding so as to have a desired shape.

Fifth Preferred Embodiment

FIGS. 16A through 16D show the fifth preferred embodiment of a fluid handling apparatus 301 according to the present invention. Furthermore, with respect to the fluid handling apparatus 301 in this preferred embodiment, the same reference numbers are given to the same structural portions as those of the fluid handling apparatus 301 in the fourth preferred embodiment to omit the duplicate descriptions thereof.

In the fluid handling apparatus 301 shown in FIGS. 16A through 16D, magnetic beads 355 to which the analyzing objects of a sample 352 adhere are mixed in the sample 352. The sample 352 containing the magnetic beads 355 is fed from the sample feeding first port 347 to the first connecting portion 307 and second connecting portion 310 via the sample feeding passage 333 and first flow passage 327 due to capillarity. The polymer solution 353 dropped into the second port 348 is fed into the end of the second flow passage 328 on the side of the first connecting portion 307 due to capillarity, and the polymer solution 354 dropped into the third port 349 is fed into the second connecting portion 310 of the third flow passage 330 due to capillarity. As this time, gas arranged between the sample 353 and the polymer solution 353 is exhausted to the external environment via the first through third sub-flow passages 341 through 343 of the first connecting portion 307 and the first external environment communication passage 331. In addition, gas arranged between the sample 352 and the polymer solution 354 is exhausted to the external environment via the fourth through sixth sub-flow passages 344 through 346 of the second communication passage 310 and the second external environment communication passage 332. As a result, the sample 352 and the polymer solutions 353, 354 can form a liquid-liquid interface level in each of the first connecting portion 307 and second connecting portion 310 while preventing gas from being mixed therein.

Thereafter, in this fluid handling apparatus 301, the magnetic beads 355 are collected into one end portion (a left end portion in FIG. 16A) of the first main flow passage 327 by a magnet (means for collecting beads) 356, so that the density of the analyzing objects adhering to the magnetic beads 355 is increased in the sample 352.

Then, in this fluid handling apparatus 301, the analyzing objects caught by the magnetic beads 355 are separated from the magnetic beads 355 by light or a remover serving as a separating means, and the concentrated analyzing objects thus separated are moved from the first main flow passage 327 to the second main flow passage 328 due to electrophoresis, so that the analyzing objects in the sample 352 are analyzed.

According to such a fluid handling apparatus 301 in this preferred embodiment, it is possible to obtain the same advantageous effects as those in the fourth preferred embodiment, and it is possible to concentrate the analyzing objects in the sample 352, so that it is possible to accurately measure and analyze the analyzing objects.

In this preferred embodiment, the position of the magnet 356 should not be limited to the end of the first main flow passage 327, but it may be suitably changed as long as the analyzing objects in the sample 352 can be efficiently concentrated.

In this preferred embodiment, the magnetic beads 355 fed into the first connecting portion 307 and the end of the first main flow passage 327 on the side of the first connecting portion 307, or into the second connecting portion 310 and the end of the first main flow passage 327 on the side of the second connecting portion 310 are caught by a gas-liquid interface level between gas and sample in the first connecting portion 307 or by a gas-liquid interface level between gas and sample in the second connecting portion 310, since the sample 352 is dammed by the first connecting portion 307 and second connecting portion 310 so as not to be discharged to the second main flow passage 328, third main flow passage 330, first external environment communication passage 331 and second external environment communication passage 332 before the polymer solutions 353 and 354 are fed into the second main flow passage 328 and third main flow passage 330. Even if the polymer solutions 353 and 354 are thus filled in the second main flow passage 328 and third main flow passage 330 to carry out electrophoresis after the first main flow passage 327 is filled with the sample 352, the diffusing speed of the magnetic beads 355 toward the second main flow passage 328 is far slower than the moving speed of the analyzing objects due to electrophoresis, so that accurate analysis is not prevented.

Sixth Preferred Embodiment

Figure 17A:
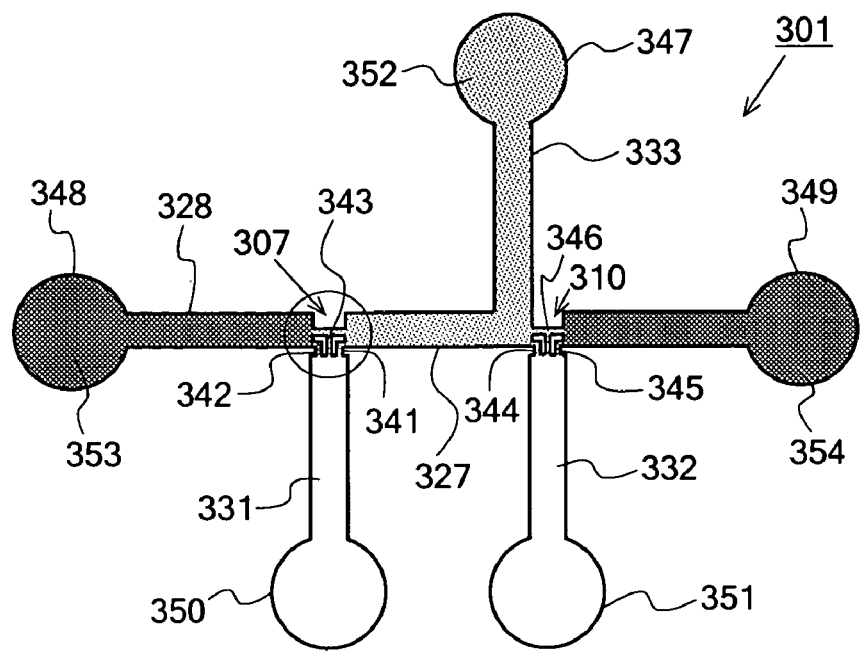
FIGS. 17A and 17B show the sixth preferred embodiment of a fluid handling apparatus according to the present invention, which correspond to FIGS. 15A and 15B.
Figure 17B:
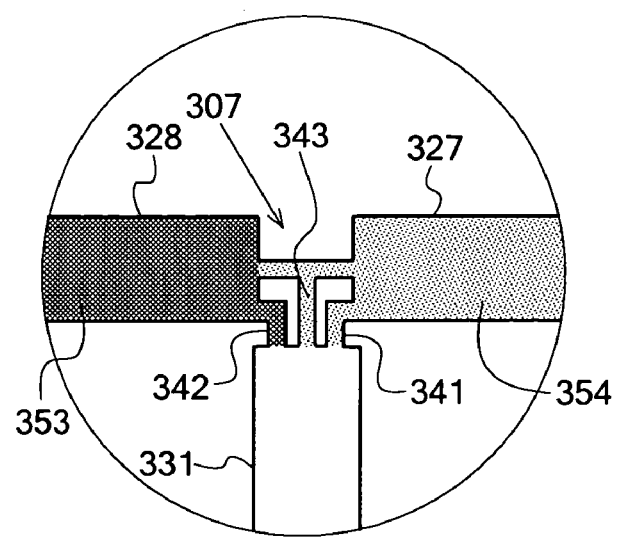

FIGS. 17A and 17B show the sixth preferred embodiment of a fluid handling apparatus 301 according to the present invention. Furthermore, with respect to the fluid handling apparatus 301 in this preferred embodiment, the same reference numbers are given to the same structural portions as those of the fluid handling apparatus 301 in the above described fourth preferred embodiment to omit the duplicate descriptions thereof.

In the fluid handling apparatus 301 in this preferred embodiment, the first and second connecting portions 307 and 310 are different from the first and second connecting portions 307 and 310 in the above described fourth and fifth preferred embodiments.

That is, as shown in FIGS. 17A and 17B, in the first and second connecting portions 307 and 310 of the fluid handling apparatus 301 in this preferred embodiment, the width of each of the first through sixth sub-flow passages 341 through 346 in directions of the width of the first member 302 (in directions perpendicular to the longitudinal directions of the first main flow passage 327 in the plan view) is decreased without decreasing the width of each of the first through sixth sub-flow passages 341 through 346 in the thickness directions of the first member 302, although the width of each of the first through sixth sub-flow passages 341 through 346 is decreased in the thickness directions of the first member 302 in the first and second connecting portions 307 and 310 in the above described fourth and fifth preferred embodiments.

In the fluid handling apparatus 301 in this preferred embodiment with such a construction, the first and second connecting portions 307 and 310 have the same liquid trapping effect as that of the first and second connecting portions 307 and 310 in the above described fourth and fifth preferred embodiments (i.e., the function of stopping a fluid at the open end of a flow passage having a small cross-sectional area to a flow passage having an abruptly enlarged cross-sectional area when the fluid flows from the flow passage having the small cross-sectional area toward the flow passage having the abruptly enlarged cross-sectional area).

Seventh Preferred Embodiment

Figure 18A:
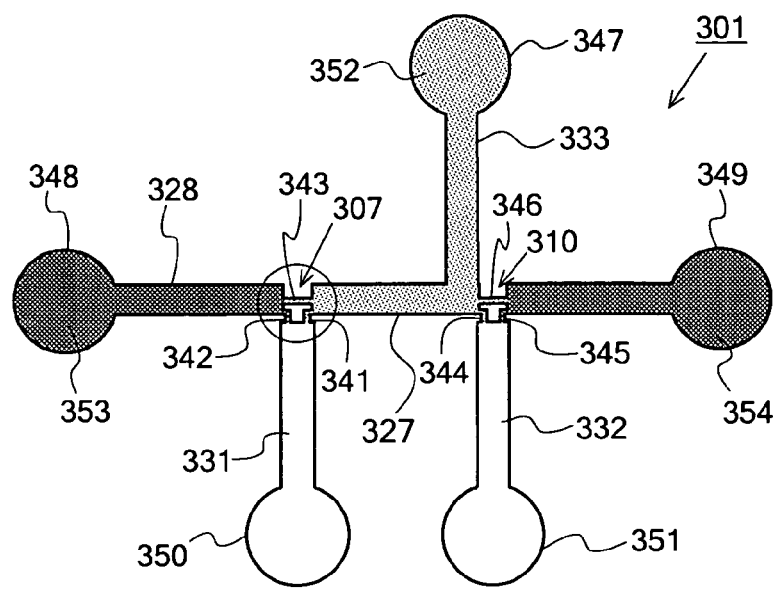
FIGS. 18A through 18C show the seventh preferred embodiment of a fluid handling apparatus according to the present invention, wherein FIGS. 18A and 18B correspond to FIGS. 15A and 15B, and FIG. 18C corresponds to FIG. 16A.
Figure 18B:
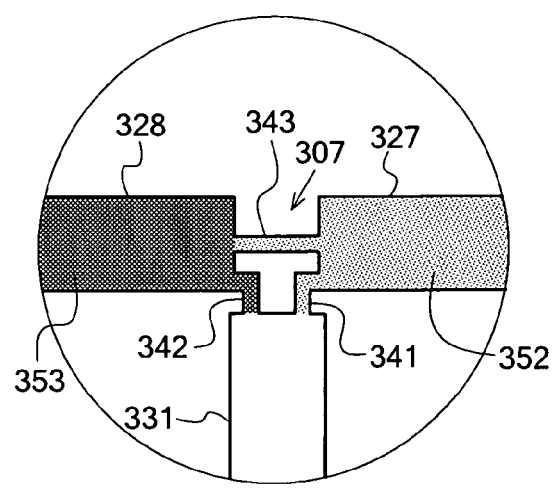
Figure 18C:
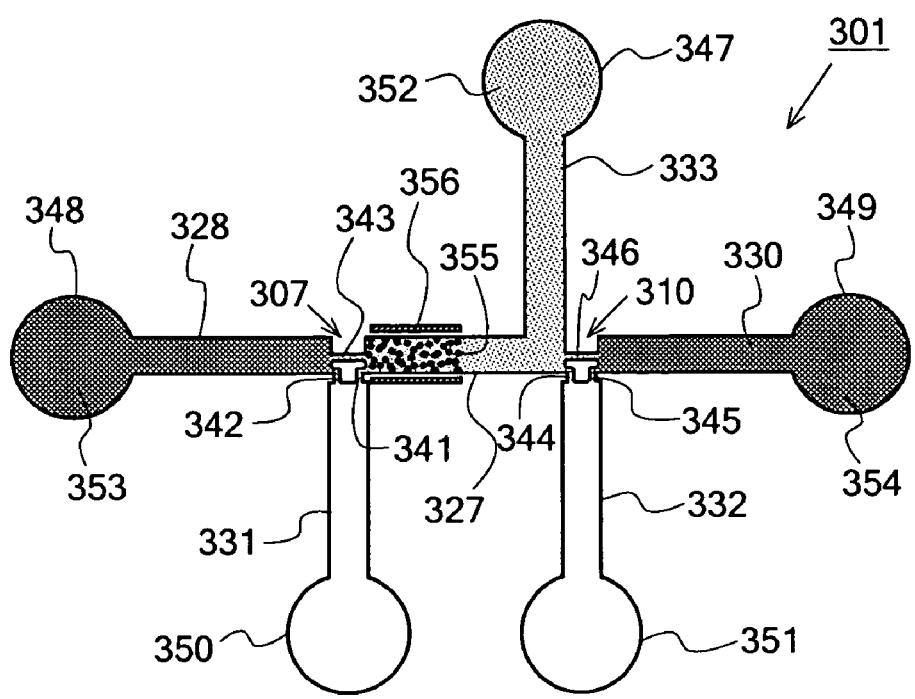
Figure 19A:
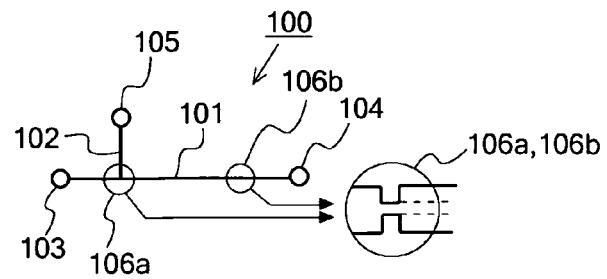
FIGS. 19A through 19F show a first example of a conventional fluid handling apparatus.
Figure 19B:
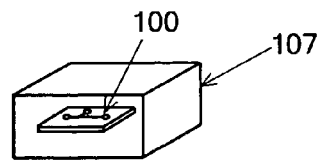
Figure 19C:
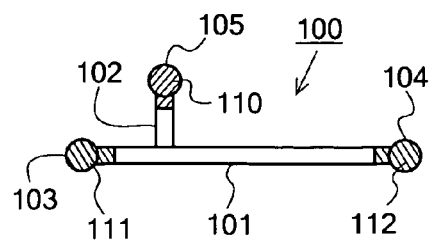
Figure 19D:
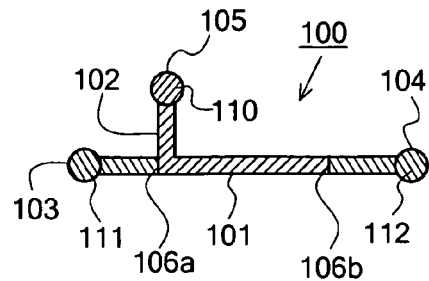
Figure 19E:
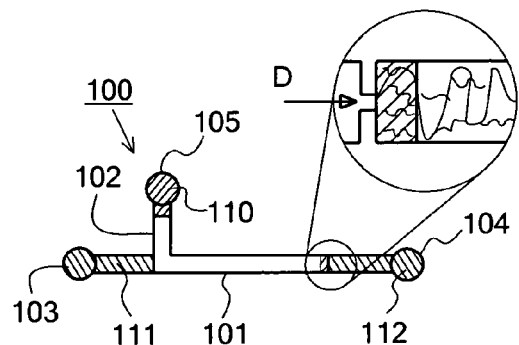
Figure 19F:
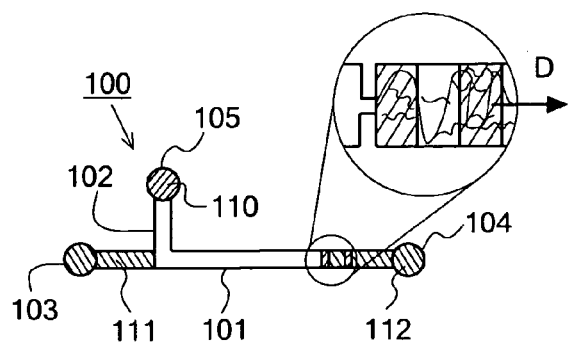
Figure 20A:
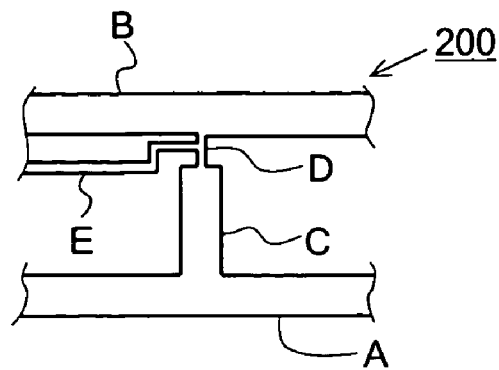
FIGS. 20A through 20D show a second example of a conventional fluid handling apparatus.
Figure 20B:
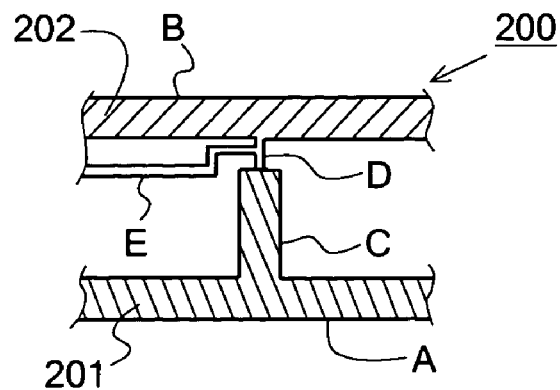
Figure 20C:
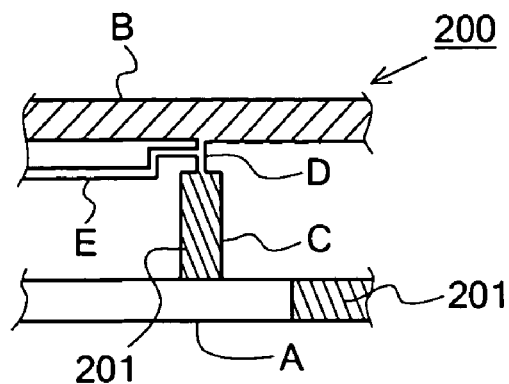
Figure 20D:
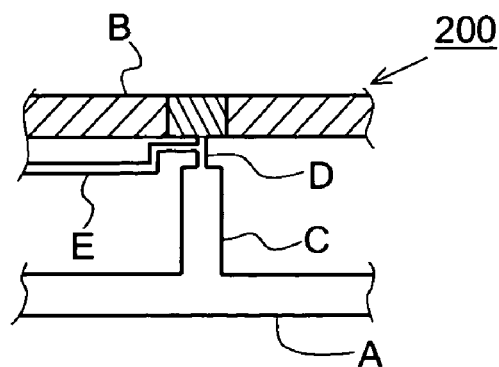

FIGS. 18A through 18C show the seventh preferred embodiment of a fluid handling apparatus 301 according to the present invention. Furthermore, the fluid handling apparatus 301 in this preferred embodiment is a modified example of a fluid handling apparatus in the above described sixth preferred embodiment, and the same reference numbers are given to the same structural portions as those of the fluid handling apparatus 301 in the above described sixth preferred embodiment to omit the duplicate descriptions thereof.

In the fluid handling apparatus 301 in this preferred embodiment, the third sub-flow passage 343 in the first connecting portion 307 and the sixth sub-flow passage 346 in the second connecting portion 310 are different from those in the above described sixth preferred embodiment.

That is, in this preferred embodiment, the third sub-flow passage 343 allows the first main flow passage 327 to be communicated with the second main flow passage 328. However, the third sub-flow passage 343 does not allow the first main flow passage 327 and the second main flow passage 328 to be communicated with the first external environment communication passage 331 unlike the third sub-flow passage 343 in the above described sixth preferred embodiment. In addition, the sixth sub-flow passage 346 allows the first main flow passage 327 to be communicated with the third main flow passage 330. However, the sixth sub-flow passage 346 does not allow the first main flow passage 327 and the third main flow passage 330 to be communicated with the second external environment communication passage 332 unlike the sixth sub-flow passage 346 in the above described sixth preferred embodiment.

Therefore, in this preferred embodiment, after the third sub-flow passage 343 of the first connecting portion and the sixth sub-flow passage 346 of the second connecting portion 310 are filled with one of the sample 352 and the polymer solution 353, 354 by feeding the polymer solutions 353 and 354 into the second main flow passage 328 and third main flow passage 330 after feeding the sample 352 into the first main flow passage 327 or by feeding the sample 352 into the first main flow passage 327 after feeding the polymer solutions 353 and 354 into the second main flow passage 328 and third main flow passage 330, it is required that the other of the sample 352 and the polymer solution 353, 354 reaches the first connecting portion 307 and second connecting portion 310.

In this preferred embodiment, if the sample 352 fed into the first main flow passage 327 and the polymer solution 353 fed into the second main flow passage 328 simultaneously reach the first connecting portion 307, gas is arranged between the sample 352 and the polymer solution 353 in the third sub-flow passage 343, so that it is difficult to form a liquid-liquid interface level in the first connecting portion 307. In addition, if the sample 352 fed into the first main flow passage 327 and the polymer solution 354 fed into the third main flow passage 330 simultaneously reach the second connecting portion 310, gas is arranged between the sample 352 and the polymer solution 354 in the sixth sub-flow passage 346, so that it is difficult to form a liquid-liquid interface level in the second connecting portion 310. Therefore, in this preferred embodiment, the timing in injecting the sample 352 into the first port 347, and the timing in injecting the polymer solution 353, 354 into the second port 348 or the third port 349 are determined so as to provide the time difference between the arrival time of the sample 352 to the first connecting portion 307 and the arrival time of the polymer solution 353 to the first connecting portion 307 and so as to provide the time difference between the arrival time of the sample 352 at the second connecting portion 310 and the arrival time of the polymer solution 354 at the second connecting portion 310.

The fluid handling apparatus 301 in this preferred embodiment has the same advantageous effects as those in the above described fourth through sixth preferred embodiments although it is required to provide the time difference in order to fill the first through third main flow passages 327, 328, 330 with the sample 352 and the polymer solutions 353, 354.

In the fluid handling apparatus 301 according to the present invention, the first connecting portion 307 in any one of the fourth, sixth and seventh preferred embodiments may be suitably combined with the second connecting portion 310 in any one of the fourth, sixth and seventh preferred embodiment.

The first and second connecting portions 307 and 310 of the fluid handling apparatus 301 according to the present invention should not be limited to those in the above described fourth through seventh preferred embodiments, but the flow passages may be throttled in the thickness and width directions of the first member 302. Also if the flow passages are thus formed, the flow passage area of each of the first through sixth sub-flow passages 341 through 346 can be abruptly decreased from the flow passage area of each of the first through third main flow passages 327, 328, 330 and the first and second external environment communication passages 331, 332 in the first and second connecting portions 307 and 310, so that the sample 352 moved by capillarity can be dammed in the first and second connecting portions 307 and 310.

While the first through third grooves 306, 308, 311, the first through sixth sub-grooves 321 through 326, the first and second external environment communication grooves 312, 313 have been formed in the reverse 303 of the first member 302 in the above described fourth through seventh preferred embodiments, the present invention should not be limited thereto, but they may be formed in the surface 305 of the second member 304 or may be divided between the reverse 303 of the first member 302 and the surface 305 of the second member 304 to be formed therein.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. A fluid handling apparatus comprising: a first flow passage capable of moving a first fluid due to capillarity; a second flow passage capable of moving a second fluid due to capillarity; and a connecting portion for allowing said first flow passage, said second flow passage and an external environment to be communicated with each other, said connecting portion comprising:

a third flow passage for allowing said first flow passage to be communicated with said external environment, said third flow passage being formed so as to be capable of moving said first fluid due to capillarity;

a fourth flow passage for allowing said second flow passage to be communicated with said external environment, said fourth flow passage being formed so as to be capable of moving said second fluid due to capillarity; and a fifth flow passage for allowing said first flow passage to be communicated with said second flow passage, said fifth flow passage having a smaller flow passage area than that of each of said first and second flow passages, and said fifth flow passage being formed so as to be capable of moving said first fluid or said second fluid due to capillarity, wherein an interface between said first fluid, which moves in said first flow passage toward said connecting portion, and said second fluid, which moves in said second flow passage toward said connecting portion, is formed in said connecting portion.

2. A fluid handling apparatus as set forth in claim 1, wherein said fifth flow passage allows said first flow passage, said second flow passage and said external environment to be communicated with each other.

3. A fluid handling apparatus comprising: a first flow passage capable of moving a first fluid due to capillarity; a second flow passage capable of moving a second fluid due to capillarity; and a connecting portion for allowing said first flow passage, said second flow passage and an external environment to be communicated with each other, said connecting portion comprising:

a fourth flow passage for allowing said second flow passage to be communicated with said external environment, said fourth flow passage being formed so as to be capable of moving said second fluid due to capillarity; and a fifth flow passage for allowing said first flow passage to be communicated with said second flow passage, said fifth flow passage having a smaller flow passage area than that of said second flow passage, and said fifth flow passage being formed so as to be capable of moving said first fluid due to capillarity, wherein an interface between said first fluid, which is injected into said first flow passage to be moved therein toward said connecting portion, and said second fluid, which is injected into said second flow passage after the injection of said first fluid to be moved therein toward said connecting portion, is formed in said connecting portion.

4. A fluid handling apparatus as set forth in claim 3, wherein said first flow passage has a first port for feeding said first fluid into said first flow passage, and said second flow passage has a second port for feeding said second fluid into said second flow passage.

5. A fluid handling apparatus comprising: a first main flow passage capable of moving a first fluid due to capillarity; a second main flow passage capable of moving a second fluid due to capillarity; a third main flow passage capable of moving a third fluid due to capillarity; a first connecting portion for allowing said first main flow passage, said second main flow passage and an external environment to be communicated with each other; and a second connecting portion for allowing said first main flow passage, said third main flow passage and said external environment to be communicated with each other, said first connecting portion comprising:

a first sub-flow passage for allowing said first main flow passage to be communicated with said external environment, said first sub-flow passage being formed so as to be capable of moving said first fluid due to capillarity;

a second sub-flow passage for allowing said second main flow passage to be communicated with said external environment, said second sub-flow passage being formed so as to be capable of moving said second fluid due to capillarity; and a third sub-flow passage for allowing said first main flow passage to be communicated with said second main flow passage, said third sub-flow passage having a smaller flow passage area than that of each of said first and second main flow passages, and said third sub-flow passage being formed so as to be capable of moving said first fluid or said second fluid due to capillarity, and said second connecting portion comprising:

a fourth sub-flow passage for allowing said first main flow passage to be communicated with said external environment, said fourth sub-flow passage being formed so as to be capable of moving said first fluid due to capillarity;

a fifth sub-flow passage for allowing said third main flow passage to be communicated with said external environment, said fifth sub-flow passage being formed so as to be capable of moving said third fluid due to capillarity; and a sixth sub-flow passage for allowing said first main flow passage to be communicated with said third main flow passage, said sixth sub-flow passage having a smaller flow passage area than that of each of said first and third main flow passages, and said sixth sub-flow passage being formed so as to be capable of moving said first fluid or said third fluid due to capillarity, wherein an interface between said first fluid, which moves in said first main flow passage toward said first connecting portion, and said second fluid, which moves in said second main flow passage toward said first connecting portion, is formed in said first connecting portion, and an interface between said first fluid, which moves in said first main flow passage toward said second connecting portion, and said third fluid, which moves in said third main flow passage toward said second connecting portion, is formed in said second connecting portion, said first fluid being metered between said first connecting portion and said second connecting portion.

6. A fluid handling apparatus as set forth in claim 5, wherein said third sub-flow passage allows said first main flow passage, said second main flow passage and said external environment to be communicated with each other, said third sub-flow passage being formed so as to be capable of moving at least one of said first and second fluids.

7. A fluid handling apparatus as set forth in claim 6, wherein said sixth sub-flow passage allows said first main flow passage, said third main flow passage and said external environment to be communicated with each other, said sixth sub-flow passage being formed so as to be capable of moving at least one of said first and third fluids.

8. A fluid handling apparatus as set forth in claim 5, wherein said first main flow passage has a first port for feeding said first fluid into said first main flow passage, said second main flow passage having a second port for feeding said second fluid into said second main flow passage, and said third main flow passage having a third port for feeding said third fluid into said third main flow passage.

9. A fluid handling apparatus as set forth in claim 8 wherein said first port is arranged in the vicinity of said first connecting portion or said second connecting portion.

10. A fluid handling apparatus as set forth in claim 5, which further comprises a potential difference applying means for applying a potential difference between said second main flow passage and said third main flow passage, to move a charged material, which is contained in said first fluid in said first main flow passage, to said second main flow passage or said third main flow passage due to electrophoresis.

11. A fluid handling apparatus as set forth in claim 1, wherein said first flow passage has a first port for feeding said first fluid into said first flow passage, and said second flow passage has a second port for feeding said second fluid into said second flow passage.

* * * * *

UNITED STATES PATENT AND TRADEMARK OFFICE
CERTIFICATE OF CORRECTION

PATENT NO. : 7,638,025 B2  Page 1 of 1
APPLICATION NO. : 11/471017
DATED : December 29, 2009
INVENTOR(S) : Koichi Ono It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 863 days.

Signed and Sealed this

Twenty-first Day of December, 2010

David J. Kappos
*Director of the United States Patent and Trademark Office*